(12) United States Patent
Chan et al.

(10) Patent No.: US 10,143,666 B2
(45) Date of Patent: Dec. 4, 2018

(54) SMALL MOLECULE INHIBITORS TARGETING CAG-REPEAT RNA TOXICITY IN POLYGLUTAMINE DISEASES

(71) Applicant: The Chinese University of Hong Kong, Shatin, N.T., Hong Kong SAR (CN)

(72) Inventors: Ho Yin Edwin Chan, Shatin (CN); Jacky Chi-Ki Ngo, Kowloon (CN); Chun-Ho Wong, Fo Tan (CN); Qian Zhang, Shatin (CN); Shaohong Peng, Shatin (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 0 days.

(21) Appl. No.: 15/382,380

(22) Filed: Dec. 16, 2016

(65) Prior Publication Data
US 2017/0181986 A1    Jun. 29, 2017

Related U.S. Application Data

(60) Provisional application No. 62/387,576, filed on Dec. 23, 2015.

(51) Int. Cl.
*A61K 31/155* (2006.01)

(52) U.S. Cl.
CPC .......... *A61K 31/155* (2013.01); *H05K 999/99* (2013.01)

(58) Field of Classification Search
CPC .................................................... A61K 31/155
See application file for complete search history.

*Primary Examiner* — Kevin E Weddington
(74) *Attorney, Agent, or Firm* — Kilpatrick Townsend & Stockton LLP

(57) ABSTRACT

The present invention provides for a novel method for treating polyglutamine (polyQ) diseases. Also disclosed are related compositions and kits for therapeutic use in the treatment of polyQ diseases.

19 Claims, 21 Drawing Sheets

The synthesis of DB213 was described in Marcheschi *et al.* (2011) Structure of the HIV-1 frameshift site RNA bound to a small molecule inhibitor of viral replication. *ACS Chem Biol* 6(8):857-64 (Scheme 1):

| Compound | IC$_{50}$ (nM) | Inhibition potency compared to DB213 (fold change) | Structure |
|---|---|---|---|
| DB213 | 6.3±0.8 | 1 | 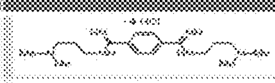 |
| DB213_D1 | Not effective | N/A | 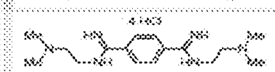 |
| DB213_D2 | 13.2±2.6 | 0.48 | 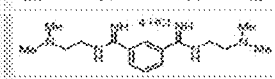 |
| DB213_D3 | 4.8±0.9 | 1.31 | 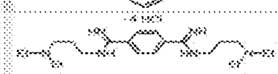 |
| DB213_D4 | 5.4±1.1 | 1.17 | 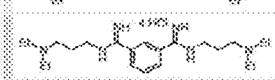 |
| DB213_D5 | 5.0±1.1 | 1.26 | 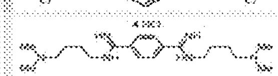 |
| DB213_D6 | 4.0±0.8 | 1.58 | 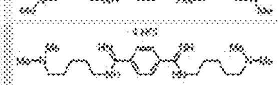 |
| DB213_D7 | Not effective | N/A | 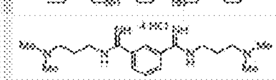 |

Figure 7

Maximum tolerance dose study on R6/2 mouse model by Charles River Company

| Mice model | Route | Compound | Dose | Dose Interval | Death (n/n) |
|---|---|---|---|---|---|
| R6/2 HD disease mouse | I.V. | DB213 | 12.5 mg/kg | Twice-a-week | 0/7 |
| | | | 25 mg/kg | | 1/8 |
| | | | 50 mg/kg | | 3/4 |
| | | | 100 mg/kg | | 2/2 |
| | | | 200 mg/kg | | 2/2 |
| | | Vehicle (ddH₂O) | Not included | | 0/7 |
| | I.N. | DB213 | 50 mg/kg | Daily for 7 days | 1/6 |
| | | | 100 mg/kg | | 2/6 |
| | | | 200 mg/kg | | 4/6 |
| | | | 300 mg/kg | | 3/6 |
| | | Vehicle (ddH₂O) | Not included | | 0/6 |

Figure 20

Study Schematic

SMALL MOLECULE INHIBITORS TARGETING CAG-REPEAT RNA TOXICITY IN POLYGLUTAMINE DISEASES

RELATED APPLICATIONS

This application claims priority to U.S. Provisional Patent Application No. 62/387,576, filed Dec. 23, 2015, the contents of which are incorporated by reference in the entirety for all purposes.

BACKGROUND OF THE INVENTION

Many neurodegenerative diseases, including Alzheimer's and Parkinson's diseases, are caused by protein misfolding. Cellular proteins that adopt abnormal pathogenic conformations oligomerize and subsequently form soluble and/or insoluble aggregates in cells causing neuronal dysfunction and death. Polyglutamine (polyQ) diseases belong to the protein misfolding disease group. It is now known that polyQ toxicity is attributed to the toxic gain-of-function nature of misfolded disease proteins that harbour the expanded polyQ domain. Unfolded protein response (UPR) is one inducible cellular protective pathway that responds to the emergence of misfolded proteins in cells. It has been reported that this mechanism is involved in neurodegenerative diseases, including polyglutamine-induced neurodegeneration. UPR can be mediated by the interaction between misfolded proteins in the endoplasmic reticulum and the molecular chaperone GRP78/BiP, and this interaction would cause the activation of UPR sensors, including activating transcription factor 6 (ATF6), inositol requiring 1 (IRE1) and PKR-like endoplasmic reticulum kinase (PERK). The induction of GRP78/BiP expression has been used as a reliable indicator of UPR. Upregulation of GRP78/Bip has been observed in polyQ degeneration, which clearly indicates the involvement of protein misfolding in polyQ pathogenesis. It is likely, however, that there are other mechanisms involved in polyQ diseases. In particular, the mRNA transcripts that encode the polyQ peptides can play a role in these diseases, especially when the mRNAs encode the polyQ portion as an expanded CAG triplet nucleotide repeat. Such expanded CAG-RNAs are known to contribute to cytotoxicity through mechanisms that are independent of polyQ-mediated cytotoxicity.

Accordingly, there is a continued need to develop new and effective methods and compositions for treating polyQ diseases by reducing or eliminating cytotoxicity induced by the expanded CAG-RNA molecules. This invention fulfills this and other related needs.

BRIEF SUMMARY OF THE INVENTION

The present inventors surprisingly discovered that certain small molecules can directly interact with CAG-repeat RNA and suppress CAG-repeat RNA toxicity. Thus, this invention provides novel methods and compositions useful for treating a polyQ disease.

In the first aspect, the present invention provides a method for treating a polyQ disease by suppressing toxicity induced by CAG-repeat RNA by administering to a patient in need thereof an effective amount of a compound of formula I:

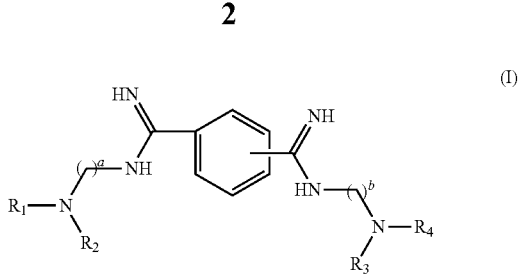

or a pharmaceutically acceptable salt, racemate, enantiomer, diastereomer, poly-morph, tautomer, geometric isomer, or prodrug thereof. Within formula I, $R^1$, $R^2$, $R^3$, and $R^4$ are each independently hydrogen, $C_{1-8}$ alkyl, of substituted $C_{1-8}$ alkyl; and subscripts a and b are each independently an integer from 1 to 8. In some embodiments, the compound is one of formula II or formula III:

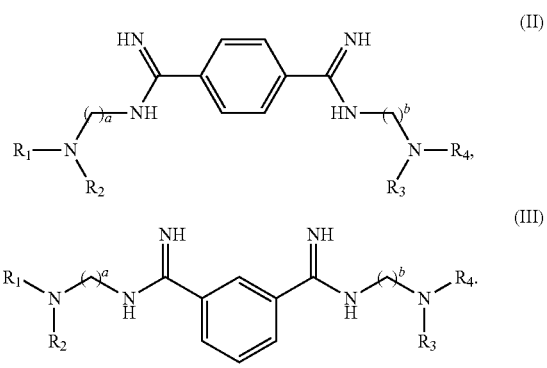

Typically, the compound is capable of inhibiting expanded CAG-RNA mediated toxicity as verified in an in vitro or in vivo assay. For example, the compound is one shown in FIG. 7: DB213, DB213_D1, DB213_D2, DB213_D3, DB213_D4, DB213_D5, DB213_D6, or DB213_D7, especially DB213, DB213_D3, DB213_D4, DB213_D5, or DB213_D6. In some embodiments, the compound is administered with another therapeutic agent effective for treating a polyQ disease. In some embodiments, the compound is administered orally or by injection, such as intravenous, intramuscular, or subcutaneous injection. In some embodiments, the compound is administered once daily, weekly, or monthly. In some embodiments, about 1-10,000 mg, about 10-1,000 mg, about 10-100 mg, about 20-50 mg, or about 10, 20, 30, 40, or 50 mg of the compound is administered each time to the subject per kg of the subject's body weight. In some embodiments, the subject is suffering from a polyQ disease or is at risk of developing a polyQ disease at a later time, such as a human patient has been diagnosed with a polyQ disease or has a known family history of a polyQ disease.

In a second aspect, the present invention provides use of a small molecule having the chemical structure of formula I, II, or III to manufacture a composition or medicament for treating a polyQ disease. The composition or medicament comprises an effective amount of a small molecule capable of suppressing toxicity induced by CAG-repeat RNA. Typically, the composition also comprises one or more physiologically acceptable excipients. In some embodiments, the medicament is formulated for injection (e.g., intravenous, intramuscular, or subcutaneous injection) or formulated for oral administration. In some embodiments, the medicament further comprises a second compound that inhibits cytotoxicity mediated by an expanded CAG-RNA or a polyQ polypeptide. In some embodiments, the medicament is formulated in a dose form containing an effective amount of the compound for one administration.

In a third aspect, the present invention provides a kit for treating a polyQ disease. The kit comprises a container containing a pharmaceutical composition comprising a compound of formula I, II, or III as described herein, which is capable of inhibiting expanded CAG-RNA mediated toxicity as verified in an in vitro or in vivo assay. In some embodiments, the kit further comprises a second pharmaceutical composition comprising a second compound effective for treating a polyQ disease. In some embodiments, the kit further comprises informational material providing instructions on administration of the pharmaceutical composition.

BRIEF DESCRIPTION OF THE DRAWINGS

FIG. 7 Comparison of the IC50 values of the DB213 derivatives.

FIG. 20 Maximum tolerance dose study on R6/2 mouse model by Charles River Company.

DEFINITIONS

Figure 1:
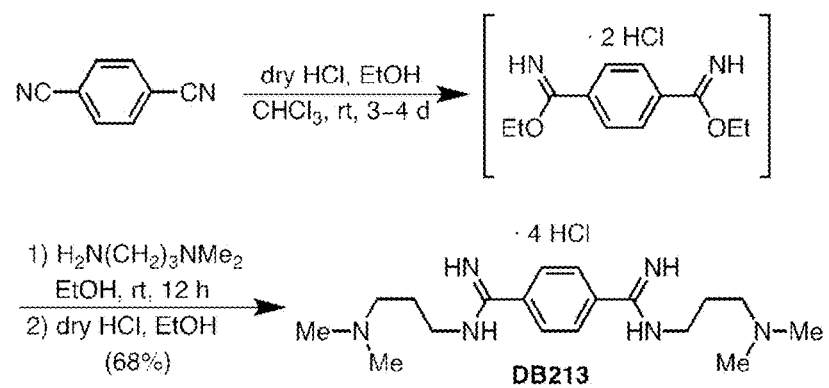
FIG. 1 Synthesis of DB213.

The term "inhibiting" or "inhibition," as used herein, refers to any detectable negative effect on a target biological process, such as expanded CAG-RNA mediated or PolyQ-mediated toxicity. Typically, an inhibition of expanded CAG-RNA mediated or PolyQ-mediated toxicity is reflected in a decrease of at least 10%, 20%, 30%, 40%, 50%, 60%, 70%, 80%, 90% or higher, including 100% or complete elimination, of one or more hallmarks of expanded CAG-RNA mediated or PolyQ-mediated toxicity as described herein, when compared to a control not given the "inhibition" treatment, such as treatment by administration of small molecule therapeutics described herein. On the other hand, inhibition of expanded CAG-RNA mediated or PolyQ-mediated toxicity may also be manifested as increased cell survival, demonstrated in an increase of at least 50%, 60%, 70%, 80%, 90%, 100%, 200%, 300%, 500% or more in the number or length of time of cell survival in the pertinent tissues within the recipient body after the small molecule administration in comparison to a control that has not received the same treatment.

As used herein, the term "treatment" or "treating" includes both therapeutic and preventative measures taken to address the presence of a disease or condition or the risk of developing such disease or condition at a later time. It encompasses therapeutic or preventive measures for alleviating ongoing symptoms, inhibiting or slowing disease progression, delaying of onset of symptoms, or eliminating or reducing side-effects caused by such disease or condition. A preventive measure in this context and its variations do not require 100% elimination of the occurrence of an event; rather, they refer to an inhibition or reduction in the likelihood or severity of such occurrence or a delay in such occurrence.

A "polyQ disease," as used herein, refers to a disease or condition that is associated with, caused by, or exacerbated by, RNA containing an expanded long repeats of CAG trinucleotides (expanded CAG-RNA) and/or polyQ polypeptides, which may be encoded by the expanded CAG-RNA. PolyQ diseases include those diseases, conditions, and symptoms that result from nucleolar stress or endoplasmic reticulum stress caused by expanded CAG-RNA, polyQ polypeptides, or both. As such, the presence of a polyQ disease can be observed at a cellular level by detecting or measuring one or more of the hallmarks of expanded CAG-RNA RNA mediated cytotoxicity or polyQ-mediated cytotoxicity. Additionally, the presence of a polyQ disease can be indicated by the presence of expanded CAG-RNA or polyQ polypeptides in pertinent cells/tissues of a person being tested for the disease. Furthermore, cells or tissues taken from or present in the body of a patient suffering from polyQ disease or suspected to suffer from a polyQ disease, e.g., due to hereditary patterns, can exhibit one or more of the hallmarks of expanded CAG-RNA mediated cytotoxicity or polyQ-mediated cytotoxicity to indicate the presence of a polyQ disease, regardless of whether clinical symptoms of the polyQ disease are apparent at the time. Exemplary polyQ diseases include Huntington's Disease (HD), Dentatorubro-pallidoluysian atrophy (DRPLA), Spinocerebellar ataxia (SCA) Type 1, Spinocerebellar ataxia Type 2, Machado-Joseph Disease (MJD/SCA3), Spinocerebellar ataxia Type 6, Spinocerebellar ataxia Type 7, Spinocerebellar ataxia Type 17, and Spinal and bulbar muscular atrophy, X-linked 1 (SMAX1/SBMA).

The term "effective amount," as used herein, refers to an amount that produces therapeutic effects for which a substance is administered. The effects include the prevention, correction, or inhibition of progression of the symptoms of a disease/condition and related complications to any detectable extent, e.g., one or more of the hallmarks of expanded CAG-RNA mediated cytotoxicity or polyQ-mediated cytotoxicity. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" when used in reference to a given value denotes a range of ±10% of the value.

As used herein, the terms "$(CAG)_n$-mediated toxicity," "expanded CAG-RNA mediated cytotoxicity," and the like refer to cytotoxicity caused by expanded CAG-RNA. Expanded CAG-RNA mediated toxicity can result in nucleolar stress and cell death. Expanded CAG-RNA mediated toxicity can be inferred by detecting or measuring one or more of (i) rRNA upstream control element hypermethylation, (ii) a decrease in rRNA transcription, (iii) a decrease in binding of NCL to the rRNA locus, (iv) an increase in binding between ribosomal proteins and MDM2, (v) stabilization of p53, (vi) accumulation of p53 in the mitochondria, (vii) release of Bcl-xL from Bak, (viii) release of cytochrome c from the mitochondria, (ix) caspase activation, and (x) apoptosis or cell death.

As used herein, the terms "PolyQ-mediated cytotoxicity," "PolyQ-mediated toxicity," and the like refer to cytotoxicity caused by polypeptides that contain polyglutamine amino acid sequences. PolyQ-mediated cytotoxicity can result in cellular stress, endoplasmic reticulum stress, an unfolded protein response, and cell death. PolyQ-mediated cytotoxicity can be inferred by detecting or measuring one or more of (i) GRP78/BiP upregulation, (ii) caspase activation, and (iii) apoptosis or cell death. PolyQ-mediated cytotoxicity can be observed independently of expanded CAG-RNA mediated cytotoxicity by measuring GRP78/BiP upregulation as explained herein. Similarly, expanded CAG-RNA mediated cytotoxicity can be observed independently of polyQ-mediated cytotoxicity by measuring one or more of rRNA hypermethylation, NCL binding to rRNA locus, the level of rRNA expression, and binding between ribosomal proteins and MDM2 as explained herein.

RNA that contains CAG triplet nucleotide repeats can cause expanded CAG-RNA mediated cytotoxicity and polyQ-mediated cytotoxicity when the CAG repeats are translated. In some cases, the CAG repeats are not in a translated region and the expanded CAG-RNA can cause expanded CAG-RNA mediated cytotoxicity but not polyQ-mediated cytotoxicity. Similarly, if a polyglutamine polypeptide is encoded by an mRNA that does not contain CAG triplet nucleotide repeats, it can cause polyQ-mediated cytotoxicity but not expanded CAG-RNA mediated cytotoxicity. For example, a polyglutamine polypeptide can be encoded by CAG/A repeats (alternating CAG and CAA, which both encode glutamine), CAA/G repeats (alternating CAA and CAG), CAA repeats, or a combination thereof. Cells that contain expanded CAG-RNA or polyQ polypeptides can be detected by detecting expanded CAG-RNA or polyQ peptide directly, or by detecting or measuring any of the hallmarks of expanded CAG-RNA toxicity or polyQ peptide toxicity.

The term a "consisting essentially of," when used in the context of describing a composition containing an active ingredient, refer to the fact that the composition does not contain other ingredients possessing any similar or relevant biological activity. For example, a composition consisting essentially of an inhibitor of expanded CAG-RNA mediated or PolyQ-mediated toxicity is a compound that does not contain other modulators such as enhancers or inhibitors of expanded CAG-RNA mediated or PolyQ-mediated toxicity.

DETAILED DESCRIPTION OF THE INVENTION

I. Introduction

Polyglutamine (polyQ) diseases are a group of late-onset, dominant genetic disorders characterized by expanded CAG repeats in the coding region of the associated genes, which are translated into expanded polyQ domains in disease proteins. Traditionally, the toxicity of polyQ disease was considered to be only caused by the expanded polyQ proteins. However, accumulating evidence demonstrate that the expanded CAG-repeat RNA is also a toxic component of polyQ pathogenesis. Recently, it was demonstrated that the expanded CAG-repeat RNA triggers nucleolar stress to induce apoptosis.

The present inventors unexpectedly discovered a small molecule, DB213, which was capable of rescuing polyQ neurodegeneration in vivo and in vitro. DB213 was first identified as frameshifting (FS) stimulator leading to the inhibition of HIV-1 replication in 1998 from a high-throughput screening. The first structural evidence that DB213 interacts with HIV-1 FS RNA was reported in 2011 (Marcheschi et al., *ACS Chem Biol* 2011 Aug. 19; 6(8):857-64. doi: 10.1021/cb200082d. Epub 2011 Jun. 15). Recently, it was shown that DB213 did not bind to CUG repeats found in the DM1 disease. Surprisingly, the inventors has revealed that DB213 interacts directly with the CAG-repeat RNA and suppresses expanded CAG-repeat RNA toxicity in both in vivo and in vitro disease models. It is further discovered that DB213 relieves the expanded CAG-repeat RNA-induced nucleolar stress in a dose-dependent manner. In addition, DB213 has relatively low cellular toxicity (no observed cytotoxicity up to 12.8 µM). It is therefore considered useful as a therapeutic agent for treating polyQ diseases.

II. Synthesis of DB213 and its Derivatives

The present invention relates to the use of small molecules such as DB213 and its structurally similar compounds or derivatives for treating a polyQ disease. Surprisingly, the inventors discovered that small molecules such as DB213 and its structural derivatives are effective for suppressing cytotoxicity induced by expanded CAG-repeat RNA. Some examples of these DB213-related small molecules and their activity are provided in FIG. 7.

DB213 and its derivatives can be readily produced according to methods known and well-practiced in the synthetic chemical and biomedical research field. For example, the chemical synthesis of DB213 has been previously described in Marcheschi et al., 2011. *ACS Chem Biol* 6(8):857-64.

Once a compound with structural similarity to DB213 is chemically synthesized, such as one generally fitting the profile of formula I, II, or III, the compound can be then tested to verify its ability to suppress or inhibit cytotoxicity induced by CAG-repeat RNA in an in vitro or in vivo assay, e.g., any one of those known in the pertinent research field or described herein. An effective compound can then be used in a therapeutic scheme for treating a patient suffering from or at risk of developing a polyQ disease, such as a human patient who has been diagnosed with a polyQ disease or who has a family history of a polyQ disease. Use of an effective compound also encompasses the use of the compound for manufacturing a medicament or a kit that is to be used for treating a polyQ disease.

III. Pharmaceutical Compositions and Administration

The present invention also provides pharmaceutical compositions or physiological compostions comprising an effective amount of a small molecule therapeutics such as DB213 and its structurally similar compounds or derivatives. Use of the compositions can be in both prophylactic and therapeutic applications for the treatment and prevention of a polyQ disease. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal administration. The preferred routes of administering the pharmaceutical compositions are intravenous or intraperitoneal delivery to a patient in need thereof (e.g., a human patient who is diagnosed of or is at risk of developing a polyQ disease) at doses of about 10-100,000 mg, 100-10,000 mg, 50-5,000 mg, 100, 200, 250, or 500 mg of each small molecule for a 70 kg adult human per day or every other day. Some exemplary doses and administration frequencies include about 1, 2, 3, 4, 5, 6, 7, 8, 9, 10, 20, 30, 40, 50, 60, 70, 80, 90, or 100 mg/kg patient body weight for each small molecule in each administration. Typically one or more small molecule therapeutics are administered to the patient either on once per day or per two-day basis. If more than one is administered, they can be administered at the same time or at separate times while all within the same general time frame. The small molecule therapeutics may be administered in a single pharmaceutical composition or they may be in multiple separate compositions. Similarly, these small molecules may be administered at the same time, or they may be administered on different days but all in close proximity to each other's administration, e.g., one administered on day 1 and other or others administered on day 2, such that the combined effects of these small molecules being co-administered are obtained. The appropriate dose may be administered in a single daily/bi-daily (once every other day) dose or as divided doses presented at appropriate intervals, for example as two, three, four, or more subdoses per day, or one dose every two, three, four, or five days.

For preparing pharmaceutical compositions of this invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., DB213 and/or its derivatives. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient (e.g., DB213 and/or its derivatives). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active component of a small molecule DB213 and/or its derivatives with encapsulating material as a carrier providing a capsule in which the small molecule (with or without other carriers) is surrounded by the carrier, such that the carrier is thus in association with the small molecule or the active component. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., DB213 and/or its derivatives) or sterile solutions of the active component in solvents comprising water, buffered water, saline, PBS, ethanol, or propylene glycol are examples of liquid compositions suitable for parenteral administration including subcutaneous, intramuscular, intravenous, or intraperitoneal administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., DB213 and/or its derivatives) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between about 3 and about 11, more preferably from about 5 to about 9, and most preferably from about 7 to about 8.

The pharmaceutical compositions one or more small molecules such as DB213 and/or its derivatives can be administered to a patient who have received a diagnosis of a polyQ disease or is at risk of developing such a disease at a later time in an amount sufficient to prevent, eliminate, reverse, or at least partially slow or arrest the symptoms of polyQ disease such as any of the clinical symptoms of the cytotoxicity related to, caused by, or enhanced by expanded CAG-repeat RNA or polyQ polypeptide. An amount adequate to accomplish this goal is defined as a "therapeutically effective dose." Amounts effective for this use will depend on the (expected) severity of the condition, route of administration, frequency of administration, and the body weight and general physical state of the patient, but generally range from about 1 mg to about 1000 mg per kg patient body weight, or about 5-500 mg/kg, about 10-100 mg/kg, about 20-50 mg/kg, e.g., about 10, 20, 25, 30, 40, 50, or 80, 100, 150, 200, or 300 mg/kg body weight for each small molecule therapeutic agent in each administration.

Single or multiple administrations of the compositions can be carried out with dose levels and pattern being selected by the treating physician. In any event, the pharmaceutical formulations should provide a quantity of DB213 and/or its derivatives sufficient to effectively inhibit the undesired symptoms in the patient relating to expanded CAG-repeat RNA or polyQ polypeptide mediated cytotoxicity. Typically, the administration lasts at least 1, 2, 3, 4, 6, 8, 10, or 12 weeks and for as long as needed such as 6 months, 1, 2, 3, 4, 5, or 10, 15, 20 years on a daily, twice a day, bi-daily (once every other day), or weekly schedule.

While other active ingredient are generally not necessary to be co-administered to a recipient with the small molecule therapeutics such as DB213 and/or its derivatives in order to treat a patient suffering from or at risk of polyQ disease, it is optional that one or more additional therapeutically effective compounds may be co-administered along with the small molecule therapeutic agent or agents, either in the same pharmaceutical composition(s) with the small molecule(s) or in a separate pharmaceutical composition. For description of other therapeutic ingredients, see, e.g., U.S. Patent Application Publication No. 2014/0357578.

IV. Kits

The invention also provides kits for treating a polyQ disease according to the method of the present invention. The kits typically include a first container that contains a pharmaceutical composition comprising a small molecule that is therapeutically effective to ameliorate the symptoms of a polyQ disease, such as DB213 or any one of its derivatives possessing a similar biological activity (e.g., capable of inhibiting cytotoxicity induced by expanded CAG-repeat RNA), optionally with an additional container that contains a pharmaceutical composition comprising another therapeutically effective compound for ameliorating the symptoms of a polyQ disease, such as another, different molecule selected from the collection of DB213 and its derivatives, or a polypeptide or polynucleotide therapeutic agent including those described in U.S. Patent Application Publication No. 2014/0357578, or any one of the known polyQ protein toxicity inhibitors such as P42, QBP1, and Congo red. In some variations of the kits, a single container may contain a pharmaceutical composition comprising two or more of compounds effective for treating a polyQ disease such as small molecules DB213 and its derivatives, those described in U.S. Patent Application Publication No. 2014/0357578, as well as inhibitors of toxicity induced by polyQ proteins. The kits may further include informational material providing instructions on how to dispense the pharmaceutical composition(s), including description of the type of patients who may be treated (e.g., human patients who have received a diagnosis of a polyQ disease or have been deemed as risk of developing a polyQ disease, e.g., due to a strong propensity indicated by family history), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Example 1: Effects of DB213 on Expanded CAG-Repeat RNA Toxicity

Introduction

Polyglutamine (polyQ) diseases consist of at least nine late-onset dominantly inherited neurodegenerative disorders, including Huntington's disease (HD), spinobulbar muscular atrophy, dentatorubral pallidoluysian atrophy and several subtypes of spinocerebellar ataxia (SCA)[1]. These diseases are characterized by expanded CAG trinucleotide repeats in the coding region of the associated genes in which the CAG triplet repeats are translated into expanded polyglutamine domains in the disease proteins. To date, there is neither a cure nor prevention, and only symptomatic treatments are available for the diseases[2]. The patients generally survive for 10 to 20 years after the diseases onset[3,4]. Evidently, there is an urgent need for the polyQ diseases therapeutic study directed at preventing or slowing the progression of neurodegeneration.

Pathogenically, the traditional hypothesis for polyQ diseases toxicity is that the expanded polyQ stretch induces neurodegeneration by triggering misfolding and aggregation of the disease proteins[5]. However, the expanded CAG-repeat RNA has also been reported as a toxic component of polyQ pathogenesis recently[6]. In order to investigate the toxic effect of expanded CAG-repeat RNA without any interference from the polyQ protein, Li et al. (2008) generated transgenic fly expressing 100 CAG repeats in the untranslated region of the DsRed reporter transgene. They demonstrated that $DsRed_{CAG100}$ fly showed late-onset progressive neurodegeneration[6]. This indicates that CAG-repeat expansion alone is capable of triggering neurodegeneration.

Recently, the inventors' research group demonstrated that the expanded CAG-repeat RNA could directly bind to nucleolin (NCL), a nucleolar protein that regulates rRNA transcription[7]. The direct interaction of expanded CAG-repeat RNA and NCL reduces rRNA levels and ribosome formation, and further leads to accumulation of unassembled ribosomal proteins. These ribosomal proteins bind to the E3 ubiquitin ligase MDM2 and trigger a chain of events ultimately leading to mitochondrial accumulation of p53 and apoptosis. This represents the nucleolar stress pathway of the expanded CAG-repeat RNA toxicity. Based on their discovery of NCL interaction with CAG-repeated RNA, the present inventors have previously developed a polypeptide or polynucleotide-based therapeutic strategy for treating polyQ diseases, see, e.g., U.S. Patent Application Publication No. 2014/0357578.

Several kinds of polyQ protein toxicity inhibitors, including P42[8], QBP1[9], and Congo red[10], have been reported to be able to inhibit the polyQ protein misfolding and aggregation both in in vitro and in vivo models. For the other toxic component of the polyQ pathogenesis, the expanded CAG-repeat RNA, have been found that can be targeted by certain small molecules and then the RNA toxicity is reduced in cell models[11]. In cell models, although the inhibitors can be evaluated by the suppressing effect on cell death or dysfunction, that is not equal to the circumstance of the whole nervous system in animal models which is much more important to the polyQ diseases therapeutic development. However, in vivo evidence of these small molecules demonstrating suppression effect of expanded CAG-repeat RNA toxicity is still lacking. The above studies prompt the present inventors to develop potent inhibitors that can suppress the expanded CAG-repeat RNA toxicity in vivo.

Results

Figure 2:
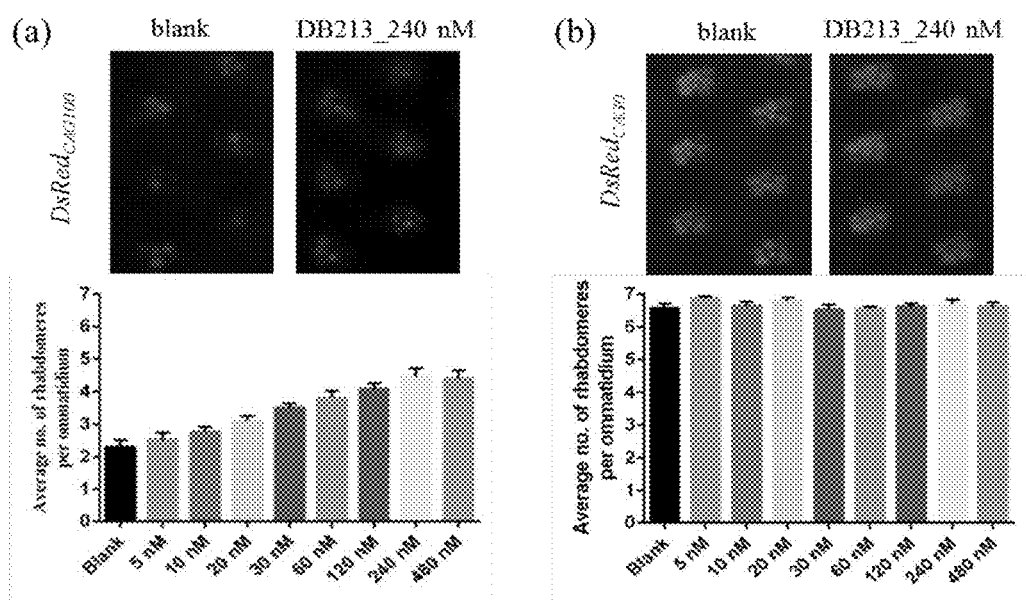
FIG. 2 (a) DB213 rescued the neurodegeneration in DsRed$_{CAG100}$ fly which only possessed RNA toxicity in a dose-dependent manner. (b) DB213 did not show dominant toxic effect on DsRed$_{CAG0}$ control fly.

The synthesis of DB213 was described in Marcheschi et al. (Scheme 1)[12], see FIG. 1. By using a MJD (one kind of polyQ diseases) Drosophila disease model, the inventors established an effective screening platform to test a series of synthesized small molecules for their activity to suppress polyQ-induced neurodegeneration. The in vivo screening result showed that three small molecules were capable of suppressing neurodegeneration (unpublished observations). To test whether the compounds acted on CAG-repeat RNA level, another Drosophila model, DsRed$_{CAG100}$[6], was employed. This transgenic fly model possesses expanded CAG repeats located in 3' untranslated region of the DsRed open reading frame. Hence, the effect of the compounds treatment on expanded CAG-repeat RNA-mediated toxicity could be studied. As previously described[6], expression of the DsRed$_{CAG100}$ transgene itself induced neurodegeneration as revealed by pseudopupil assay (FIG. 1a). One of the compounds, DB213, suppressed the DsRed$_{CAG100}$ RNA-mediated toxicity in a dose-dependent manner (FIG. 2a). Also, DB213 did not show any dominant toxic effect in the control fly, DsRed$_{CAG0}$ (FIG. 2b). Therefore, DB213 was confirmed to modulate expanded CAG-repeat RNA-mediated toxicity in vivo.

Figure 3:
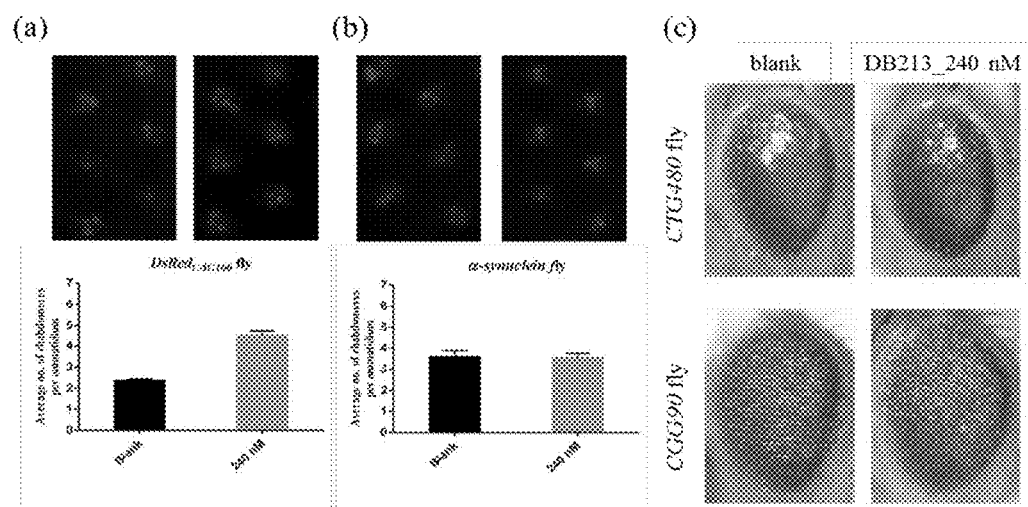
FIG. 3 (a) DB213 rescued the neurodegeneration in DsRed$_{CAG100}$ fly. (b) DB213 did not suppress the neurodegeneration in α-synuclein fly. (c) DB213 did not suppress the neurodegeneration in CTG480 & CGG90 flies.

Other disease fly models, including α-synuclein (Parkinson's disease)[13], CTG480 (Myotonic dystrophy 1)[14] and CGG90 (Fragile X syndrome)[15] were employed to address the specificity of DB213 on trinucleotide repeat expansion RNA toxicity. Consistent with previous reports, these models both showed degenerative phenotypes (FIG. 3b, c). However, DB213 did not suppress the neurodegeneration in these flies (FIG. 3b, c). Therefore, this indicates that the suppressive effect of DB213 is specific for expanded CAG-repeat RNA-mediated toxicity in vivo.

Figure 4:
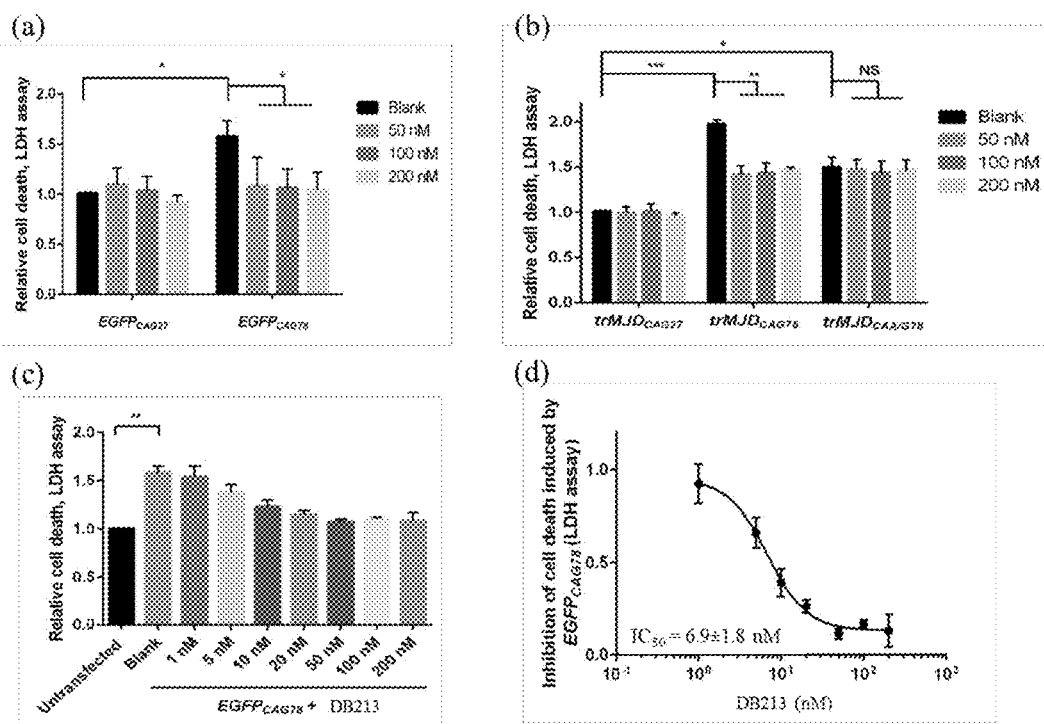
FIG. 4 (a) DB213 inhibited cell death in EGFP$_{CAG78}$ RNA expressing SK-N-MC cells. (b) DB213 only partially inhibited the cell death in trMJD$_{CAG78}$ cells which possessed both trMJD$_{CAG78}$ RNA and trMJDQ78 protein toxicities, and did not alter the cell death level in trMJD$_{CAA/G78}$ cells which only possessed trMJDQ78 protein toxicity. (c) DB213 inhibited cell death induced by EGFP$_{CAG78}$ RNA in a dose-dependent manner. (d) IC$_{50}$ value of DB213, calculated based on (c), represents the concentration of DB213 that reduced LDH enzyme activity by 50% when compared with the no treatment control group.

It was next investigated whether DB213 could mitigate expanded CAG-repeat RNA-mediated toxicity in SK-N-MC human neuronal cell. By means of the lactate dehydrogenase (LDH) cytotoxicity assay[16], the SK-N-MC cells expressing expanded CAG RNA, EGFP$_{CAG78}$, showed a relatively higher level of cell death, compare with the unexpanded control—EGFP$_{CAG27}$—expressing cells, and the cell death induced by EGFP$_{CAG78}$ RNA could be suppressed by DB213 (FIG. 4a). Moreover, based on the result of the LDH cytotoxicity assay (FIG. 4b), DB213 only partially inhibited the abnormal cell death in trMJD$_{CAG78}$ cell model which possessed both trMJD$_{CAG78}$ RNA and trMJDQ78 protein toxicities, and did not alter the cell death level in trMJD$_{CAA/G78}$ cell model, which only possessed trMJDQ78 protein toxicity. Taken together, DB213 could suppress the expanded CAG RNA-mediated but not polyQ protein-mediate toxicity in human neuronal cell. As a step further, the inventors showed that cell death induced by EGFP$_{CAG78}$ RNA could be inhibited by DB213 in a dose-dependent manner (FIG. 4c) and the calculated half maximal inhibitory concentration (IC$_{50}$) value was 6.9±1.8 nM (FIG. 4d).

Figure 5:
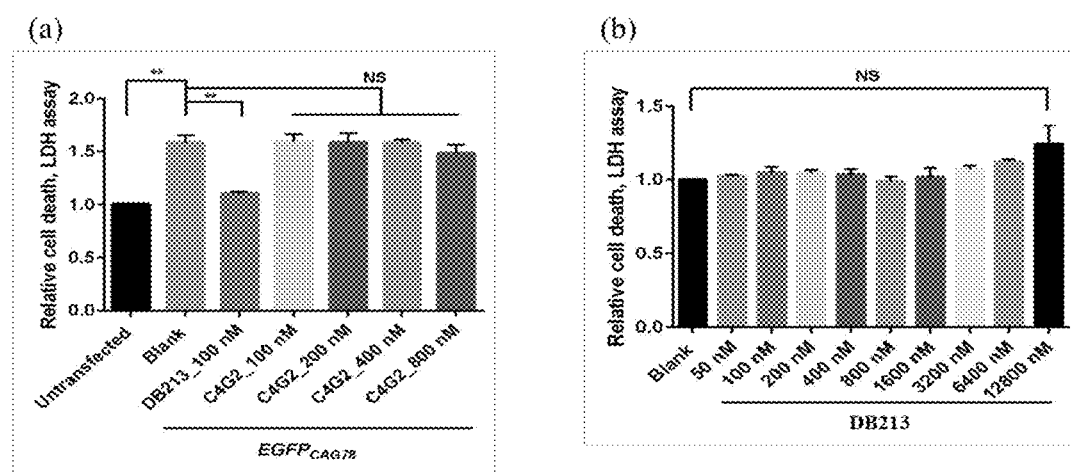
FIG. 5 (a) C4G2 did not inhibit cell death induced by EGFP$_{CAG78}$ RNA. (b) DB213 did not show dominant toxic effect on primary rat cortical neurons.

To address the specificity of DB213 on expanded CAG-repeat RNA toxicity in vitro, another small molecule compound, C4G2, labeled as ligand 3 in the study[17], was employed. C4G2 was reported to be capable of binding to CUG-repeat RNA directly and tightly, suppressing the CUG-repeat RNA toxicity in in vitro and in vivo myotonic dystrophy 1 disease models. Based on the inventors' observation, the EGFP$_{CAG78}$ RNA-induced cell death could be suppressed by DB213, however, could not be rescued by C4G2 (FIG. 5a). This indicates that DB213 specifically mitigated expanded CAG-repeat RNA toxicity in this cell model. Also, the cytotoxicity test on primary rat cortical neurons showed that the viability of the wild-type primary neurons was not compromised when they were treated with up to 12,800 nM of DB213 (FIG. 5b). This clearly demonstrated that DB213 per se does not elicit observable dominant toxic effect on mammalian neurons at micromolar concentrations.

It was next investigated that whether DB213 would interact physically with CAG-repeat RNA and sequestrate the toxic RNA species from their pathogenic pathway. Isothermal titration calorimetry (ITC)[17] was adopted to identify the RNA-binding property of DB213. It was discovered that DB213 bound to CAG-repeat RNA, r(CAG)$_7$, with a very low K$_D$ value (1.53±0.25 μM; FIG. 6a). This result indicates that there was a direct interaction between DB213 and CAG-repeat RNA.

Based on the inventors' recent study, the expanded CAG-repeat RNA bound directly to the nucleolin (NCL) protein, and this interaction caused hypermethylation of the upstream control element (UCE) in the rRNA promoter and resulted in down-regulation of pre-45s rRNA transcription. Nucleolar stress and a chain of downstream events were triggered and ultimately led to apoptosis[7]. The inventors showed that DB213 could restore the pre-45s rRNA transcription level which was reduced by expanded CAG-repeat RNA, EGFP$_{CAG78}$ in a dose-dependent manner in SK-N-MC neuronal cells (FIG. 6b). Also, DB213 did not alter the pre-45s rRNA transcription level in EGFP$_{CAG27}$ RNA expressing cell (FIG. 6b). This indicates that DB213 could mitigate the expanded CAG-repeat RNA toxicity in the nucleolar stress pathway.

Furthermore, a series of DB213 derivatives were generated, including DB213_D1 to D7, and then the IC$_{50}$ values of the derivatives were determined by LDH assay in EGFP$_{CAG78}$-expressing SK-N-MC cells. Among all the derivatives, compared with DB213, DB213_D1 and DB213_D7 did not rescue the cell death induced by EGFP$_{CAG78}$ RNA (FIG. 7). However, the other derivatives were able to suppress the cell death induced by EGFP$_{CAG78}$ RNA and the IC$_{50}$ values of these derivatives were similar to the IC$_{50}$ of DB213 (FIG. 7). This strongly demonstrates that DB213 is a representative of a series of similar structures that could suppress the expanded CAG-repeat RNA-mediated toxicity.

Figure 6:
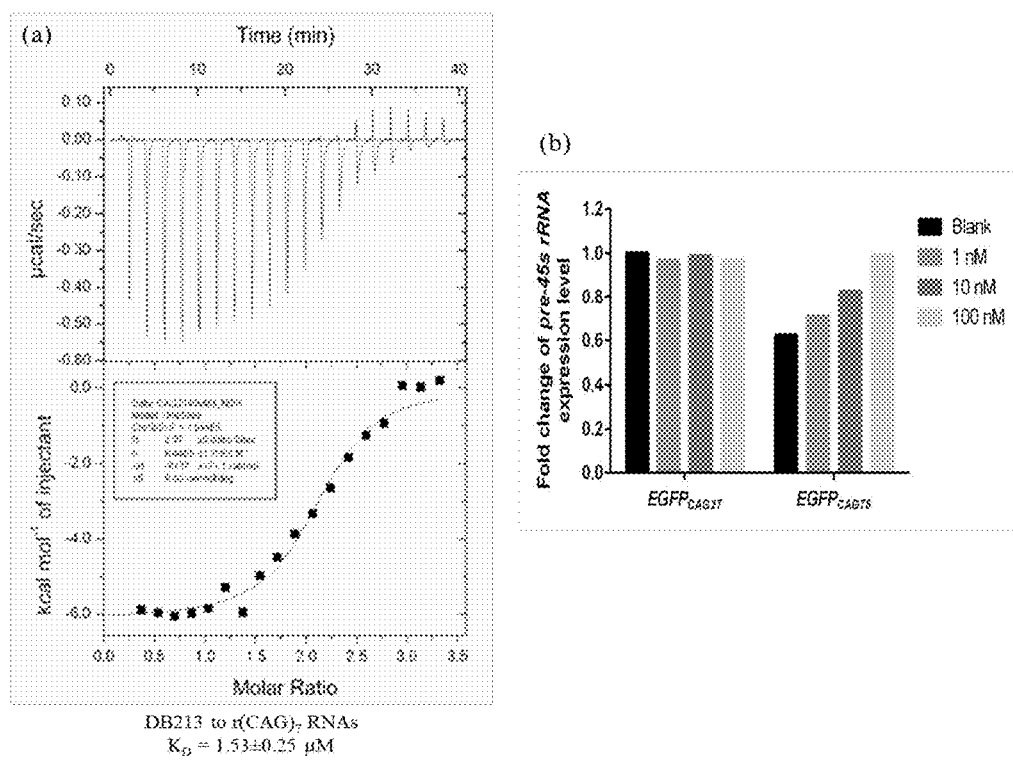
FIG. 6 (a) Isothermal titration calorimetry study of the binding of DB213 (800 μM) to synthesized r(CAG)$_7$ RNA (40 μM). DB213 bound to CAG-repeat RNA, r(CAG)$_7$, with a low micromolar $K_D$ value (1.53±0.25 μM). (b) DB213 restored the expression level of pre-45s rRNA in EGFP$_{CAG78}$ RNA expressing SK-N-MC cells in a dose-dependent manner.
Figure 8:
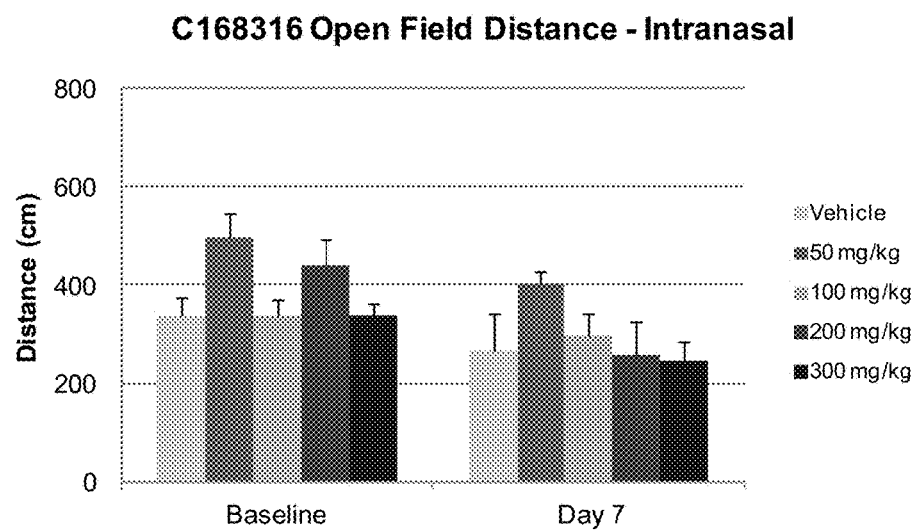
FIG. 8 Open field distance. Group mean+SEM. *p<0.05 vs. respective vehicle group.

Experimental data showed that DB213 suppressed the expanded CAG-repeat RNA-mediated toxicity in both in vivo and in vitro disease models (FIGS. 2-5). It was also revealed that DB213 could directly bind to CAG-repeat RNA and relieve the expanded CAG-repeat RNA-induced nucleolar stress in a dose-dependent manner (FIG. 6). Furthermore, most of the DB213 derivatives were able to suppress the expanded CAG-repeat RNA-mediated toxicity (FIG. 7). Taken together, this series of small molecules are potent inhibitors against the expanded CAG-repeat RNA-mediated toxicity in polyQ diseases and are therefore useful as therapeutic agents for polyQ diseases.

Methods

Examination of Drosophila Adult Eyes by Pseudopupil Assay and External Eye Assay Flies were raised at 21.5° C. on cornmeal medium supplemented with dry yeast. Pseudopupil assay was performed on 12 day-old adult flies as mentioned previously[18]. Images were captured by SPOT Insight CCD camera controlled by the SPOT Advanced software (Diagnostic instruments Inc.). External eye assay was performed on 12 day-old adult flies by Olympus SZX-12 stereomicroscope. Eye images were captured using a SPOT Insight CCD camera (Diagnostic instruments Inc.).

Lactate Dehydrogenase (LDH) Cytotoxicity Assay

SK-N-MC human neuronal cells were seeded on a 24-well plate and lactate dehydrogenase enzyme activity in the cell culture medium was measured 72 hours post-transfection and drugs treatment using the Cytotox 96 non-radioactive cytotoxicity assay (Promega).

Isothermal Titration Calorimetry (ITC) Binding Assay

Experiments were carried out using a MicroCal iTC200 isothermal titration calorimeter (GE Healthcare) at 25° C. Data were analyzed using the Origin® scientific plotting software version 7 (Microcal Software Inc.). DB213 (800 μM) was titrated to synthesized r(CAG)$_7$ RNA (40 μM). The thermal titration data were fitted to the 'one binding site model' to determine the dissociation constant ($K_D$).

RNA Extraction, Reverse Transcription and Real-Time PCR

RNA was extracted from cells by Trizol reagent (Life Technologies), and 1 μg of purified RNA was then used for reverse-transcription using the ImPromII™ Reverse Transcription System (Promega). Random hexamer (Roche) was used as primers in reverse transcription. Taqman gene expression assays were performed on an ABI 7500 Real-time PCR system and data were analyzed as previously described[7]. The following probes were used: pre-45s rRNA (Assay ID: AILJIZM) and actin (Assay ID: Hs99999903_m1).

Example 2: Tolerability of DB213 in R6/2 Huntington's Mice after i.n. or i.v. Dosing Summary Purpose—

The objective of this study was to investigate the tolerability of i.n. or i.v. administrated Compound-5 (DB213) treatment on 1) neurological index (NI) scores, 2) body weight, 3) body temperature and 4) activity in open field test in R6/2 Huntington's mice.

Methods—

All animal experiments were carried out according to the National Institute of Health (NIH) guidelines for the care and use of laboratory animals, and approved by the National Animal Experiment Board. 60 male and female R6/2 TG mice received from JAX were used for the study. Following treatment groups were used:

i.n.: Group 1: 3 female and 3 male R6/2 mice treated with i.n. vehicle starting at 6 weeks of age and continuing for 7 days; Group 2: 3 female and 3 male R6/2 mice treated i.n. daily with Compound-5 at 50 mg/kg starting at 6 weeks of age and continuing for 7 days; Group 3: 3 female and 3 male R6/2 mice treated i.n. daily with Compound-5 at 100 mg/kg starting at 6 weeks of age and continuing for 7 days; Group 4: 3 female and 3 male R6/2 mice treated i.n. daily with Compound-5 at 200 mg/kg starting at 6 weeks of age and continuing for 7 days; Group 5: 3 female and 3 male R6/2 mice treated i.n. daily with Compound-5 at 300 mg/kg starting at 6 weeks of age and continuing for 7 days.

i.v.: Group 6: 2 female and 5 male R6/2 mice treated with i.v. vehicle twice-a-week starting at 6 weeks of age and continuing for 7 days; Group 7: 2 female and 5 male R6/2 mice treated i.v. twice-a-week with Compound-5 at 12.5 mg/kg starting at 6 weeks of age and continuing for 7 days; Group 8: 3 female and 5 male R6/2 mice treated i.v. twice-a-week with Compound-5 at 25 mg/kg starting at 6 weeks of age and continuing for 7 days; Group 9: 4 female R6/2 mice treated i.v. twice-a-week with Compound-5 at 50 mg/kg starting at 6 weeks of age and continuing for 7 days (treatment discontinued); Group 10: 2 female R6/2 mice treated i.v. twice-a-week with Compound-5 at 100 mg/kg starting at 6 weeks of age and continuing for 7 days (treatment discontinued); Group 11: 2 female R6/2 mice treated i.v. twice-a-week with Compound-5 at 200 mg/kg starting at 6 weeks of age and continuing for 7 days (treatment discontinued).

The body weights were measured daily. Neurological index was scored on day 1 (baseline), and on days 3, 5 and 7. Body temperature was measured from rectum on day 1 (baseline), and on days 3, 5 and 7. Open field test was performed at day 0 (baseline assessment), and on day 7.

Results—Intranasal Dosing.

There were no differences in body weight between the treatment groups at any of the time points. In total 10 mice were lost from the following treatment groups: 1 mouse from 50 mg/kg group (16.7%), 2 mice from 100 mg/kg group (33.3%), 4 mice from 200 mg/kg group (66.7%), and 3 mice from 300 mg/kg group (50%). There were no differences in open field distance, rearings, distance in center, rearings in center or velocity between the intranasal treatment groups on day 7. When the mean neurological index score of all parameters was analyzed, a significant difference was found on day 3; 300 mg/kg treatment group had significantly higher mean score on day 3 compared to vehicle group. On day 7 the body temperature was increased in both 100 and 300 mg/kg treatment groups compared to vehicle.

Intravenous Dosing.

There were no differences in body weight between the treatment groups at any of the time points. Groups 50, 100 and 200 mg/kg were not used in statistical analysis due to mortality and low animal numbers. In total 8 mice were lost from the following treatment groups: 1 mouse from 25 mg/kg group (12.5%), 3 mice from 50 mg/kg group (75%) (treatment was discontinued for one remaining mouse in 50 mg/kg group), 2 mice from 200 mg/kg group (100%), and 2 mice from 300 mg/kg group (100%). There were no differences in open field distance, rearings, distance in center, rearings in center or velocity between the intravenous treatment groups on day 7. There were no differences in neurological index score between the intravenous treatment groups. There were no significant differences in body temperature between the intravenous treatment groups.

Conclusions—

These results show that both intranasal and intravenous treatment with Compound-5 in R6/2 mice of Huntington's disease increase mortality in dose-dependent manner. The compound has no effect on movement activity in open field test on day 7 post-dosing. However, intranasal dosing of Compound-5 increased neurological index score and body temperature. These result suggest that the highest tolerated dose for Compound-5 could be 50-100 mg/kg intranasally and 12.5-25 mg/kg intravenously.

Materials and Methods

Animals

All animal experiments were carried out according to the National Institute of Health (NIH) guidelines for the care and use of laboratory animals, and approved by the National Animal Experiment Board. 60 male and female R6/2 TG mice (stock #006494; 120+/−5 CAG repeat expansions) received from JAX were used for the study.

Following treatment groups were used:
i.n.:
- Group 1: 3 female and 3 male R6/2 mice treated with i.n. vehicle starting at 6 weeks of age and continuing for 7 days
- Group 2: 3 female and 3 male R6/2 mice treated i.n. daily with Compound-5 at 50 mg/kg starting at 6 weeks of age and continuing for 7 days
- Group 3: 3 female and 3 male R6/2 mice treated i.n. daily with Compound-5 at 100 mg/kg starting at 6 weeks of age and continuing for 7 days
- Group 4: 3 female and 3 male R6/2 mice treated i.n. daily with Compound-5 at 200 mg/kg starting at 6 weeks of age and continuing for 7 days
- Group 5: 3 female and 3 male R6/2 mice treated i.n. daily with Compound-5 at 300 mg/kg starting at 6 weeks of age and continuing for 7 days i.v.:
- Group 6: 2 female and 5 male R6/2 mice treated with i.v. vehicle twice-a-week starting at 6 weeks of age and continuing for 7 days
- Group 7: 2 female and 5 male R6/2 mice treated i.v. twice-a-week with Compound-5 at 12.5 mg/kg starting at 6 weeks of age and continuing for 7 days
- Group 8: 3 female and 5 male R6/2 mice treated i.v. twice-a-week with Compound-5 at 25 mg/kg starting at 6 weeks of age and continuing for 7 days
- Group 9: 4 female R6/2 mice treated i.v. twice-a-week with Compound-5 at 50 mg/kg starting at 6 weeks of age and continuing for 7 days (treatment discontinued)
- Group 10: 2 female R6/2 mice treated i.v. twice-a-week with Compound-5 at 100 mg/kg starting at 6 weeks of age and continuing for 7 days (treatment discontinued)
- Group 11: 2 female R6/2 mice treated i.v. twice-a-week with Compound-5 at 200 mg/kg starting at 6 weeks of age and continuing for 7 days (treatment discontinued)

Husbandry

All mice were housed in groups of up to 4 per cage (mixed genotypes, single sex), in a temperature (22±1° C.) and humidity (30-70%) controlled environment with a normal light-dark cycle (7:00-20:00). All mice were housed in cages with clean bedding covering the ground that was changed as frequently as needed to provide the animals with dry bedding. This basic environment was enriched with the addition of play tunnels, wooden nesting material, and plastic bones for all mice; i.e. an environmentally-enriched cage contains a Mouse Tunnel, (amber color, certified, transparent, BioSery Product# K3323) and a Petite Green Gumabone (BioSery Product # K3214). Food (Purina Lab Diet 5001) and water were available ad libitum to the mice in their home cages. R6/2 mice also received wet powdered food (Purina Lab Diet 5001 mixed with water to form a paste) placed inside a cup on the floor of the cage; this additional food was replaced fresh daily and started at arrival of mice. In addition, water spouts were fitted with extensions to allow mice to easily access from floor level.

Experimental Set Up of Mice

In setting up groups for study (i.e. vehicle or compound treated), transgenic mice were randomized into groups so that whole litters of mice did not end up in a single testing group. Mice were allowed to acclimate to the experimental room for at least one hour prior to the beginning of any experiment. Mice were transported from the colony room to experimental rooms in their home cages. Experimentation was conducted in a blinded manner.

Compound Delivery and Formulation

Compound-5 or vehicle was administered i.n. daily or i.v. twice-a-week starting at 6 weeks of age for 7 days.

i.v. administration: mice received 2 weekly i.v. injections into the tail vein. Mice were weighed on each treatment day and the dose adjusted accordingly to 1 ml/kg dose volume. For example, a mouse with a 30 g body weight received an i.v. injection of 30 µl. The whole i.v. injection process took 5-8 min per mouse.

i.n. administration: using a three fingered scruff, each mouse was restrained twice and held with neck parallel to the table while the compound was administered. The volume was 0.56 ml/kg. For example, a mouse with a 30 g body weight received in total 16.8 µl. During each restraint, 8.4 µl was administered to the left nostril as two 4.2 µl drops, followed by a 15 sec hold, and 8.4 µl was administered to the right nostril as two 4.2 µl drops, followed by a 15 sec hold. Notes were taken on the success of delivery and any lost volume greater than 2 µl were re-administered.

Body Weight

The body weights were measured daily.

Neurological Index

The mice were observed for 1-2 minutes per mouse on days 1 (baseline), 3, 5 and 7. The following 30 behaviors were evaluated: Head Tremor, Head Twitch, Head Bobbing, Head Searching, Body Tremor, Body Twitch, Tail Tremor, Tail Twitch, Straub Tail, Piloerection, Shallow Respiration, Flattened Body Posture, Swollen Face, Ptosis, Irritability, Seizure, Urine Staining, Lacrimation, Salivation, Limb Splay, Catalepsy, Abnormal Gait, Tip Toe Walking, Slow Careful Movements, Excessive Grooming, Circling, Sniffing, and Chewing. In addition to the above occurrences the chronic observational phase included excessive locomotor activity, loss of startle response, loss of righting reflex, dehydration and tail pinch. The assessment was performed as follows: A score of 0 was assigned for normal features (such as locomotor activity) or for the absence of abnormal features (such as absence of piloerection); a score of 1 was given when mild abnormalities were observed; and a score of 2-3 was given when severe abnormalities were observed. All of these features were scored from simple observation of the mice in their cage, except for the startle, tail pinch and righting reflexes which were direct manipulations. To test the startle reflex, a small hand clicker was used to generate a loud popping noise and the following behaviors were identified during this process: jumping, freezing, and rapid eye blinks. For the righting reflex, each mouse was then removed from its home cage and placed on its back allowing the mouse to correct itself. Tail pinch was tested by gently squeezing the end of the tail with forceps.

Body Temperature

Body temperature was measured from rectum on day 1 (baseline) and on days 3, 5 and 7.

Open Field

Open field test was performed at baseline, and on day 7. The mice were brought to the experimental room for at least 1 h acclimation to the experimental room conditions prior to testing. Activity chambers (Med Associates Inc, St Albans, Vt.; 27×27×20.3 cm) were equipped with IR beams. Mice were placed in the center of the chamber and their behavior was recorded for 30 min in 5-minute bins. Quantitative analysis was performed on the following five dependent measures: total locomotion, locomotion in the center of the open field, rearing rate in the center, total rearing frequency and velocity. Animals were tested at low-stress conditions where the light was lowered to approximately 10-30 lux of red light.

End-Point and Tissue Processing

No tissue samples were collected.

General Health Status and Humane End-Points

Animals were monitored twice-a-day by laboratory personnel (8 am and 16 μm). In case general health status of an animal was significantly worsened, the mouse was euthanized by an overdose of $CO_2$ and decapitated. Definitions of acceptable endpoints included: no spontaneous movements and inability to drink or eat in 24-h observation period, massive bleeding, spontaneous inflammation, missing anatomy, swelling or tumors larger than 20 mm, and inability to right itself in 30 sec period.

All animals were monitored over the course of the study for any potential adverse events related treatment, or occurring at a higher incidence in treated animals. Any adverse events potentially related to treatment were documented and described with respect to when events were observed.

Statistical Analysis

All values were presented as mean±standard error of mean (SEM), and differences were considered to be statistically significant at the $p<0.05$ level. Statistical analysis was performed using StatsDirect statistical software. Differences between group means are analyzed by 1-way-ANOVA followed by Dunnett's test (comparison to the control (=vehicle treated R6/2 mice) group).

Results

Body Weight and Mortality

Intranasal Dosing.

There were no differences in body weight between the treatment groups at any of the time points ($p>0.05$) (Table 1). In total 10 mice were lost from the following treatment groups: 1 mouse from 50 mg/kg group (16.7%), 2 mice from 100 mg/kg group (33.3%), 4 mice from 200 mg/kg group (66.7%), and 3 mice from 300 mg/kg group (50%).

TABLE 1

Body weight in intranasal dosing groups

| Treatment | Gender | Mouse ID | Day 1 | Day 2 | Day 3 | Day 4 | Day 5 | Day 6 | Day 7 |
|---|---|---|---|---|---|---|---|---|---|
| Vehicle | Female | 1 | 19.2 | 18.8 | 19.2 | 18.7 | 18.5 | 18.9 | 19.3 |
| | | 6 | 19.6 | 19.5 | 19.3 | 19.1 | 18.5 | 18.3 | 19 |
| | | 11 | 20.7 | 20.7 | 21.7 | 21.3 | 20.9 | 21 | 21.4 |
| | Male | 16 | 24.5 | 24.2 | 24.6 | 24.9 | 24.4 | 24.7 | 25 |
| | | 21 | 22.9 | 23 | 23 | 22.8 | 21.4 | 21.8 | 21.9 |
| | | 26 | 24.6 | 25 | 25 | 24.7 | 24.5 | 24.3 | 24.9 |
| | | Mean | 21.9 | 21.9 | 22.1 | 21.9 | 21.4 | 21.5 | 21.9 |
| | | SD | 2.4 | 2.6 | 2.5 | 2.7 | 2.7 | 2.7 | 2.6 |
| | | SEM | 1.0 | 1.0 | 1.0 | 1.1 | 1.1 | 1.1 | 1.1 |
| | | n | 6 | 6 | 6 | 6 | 6 | 6 | 6 |
| 50 mg/kg | Female | 2 | 20.9 | 20.6 | 21.1 | 20.1 | 19.9 | 19.9 | 20.4 |
| | | 7 | 20 | 17.9 | | | | | |
| | | 12 | 18.1 | 17.5 | 18.1 | 18.1 | 17.4 | 17.6 | 17.9 |
| | Male | 17 | 23.9 | 23.3 | 24 | 23.8 | 23.6 | 23.4 | 23.5 |
| | | 22 | 21.8 | 21.7 | 21.4 | 21.9 | 20.7 | 21.5 | 21.5 |
| | | 27 | 25.8 | 25.3 | 26.3 | 26.3 | 25.6 | 25 | 26.3 |
| | | Mean | 21.8 | 21.1 | 22.2 | 22.0 | 21.4 | 21.5 | 21.9 |
| | | SD | 2.8 | 3.0 | 3.1 | 3.2 | 3.2 | 2.9 | 3.2 |
| | | SEM | 1.1 | 1.2 | 1.4 | 1.4 | 1.4 | 1.3 | 1.4 |
| | | n | 6 | 6 | 5 | 5 | 5 | 5 | 5 |
| 100 mg/kg | Female | 3 | 19 | 18.7 | 19.3 | 19.4 | 18.8 | 19.1 | 19 |
| | | 8 | 20.6 | 20.3 | 20.7 | 20.8 | 20.6 | | |
| | | 13 | 21.2 | 19.2 | 19.8 | 19.8 | 19.4 | 19.8 | 19.4 |
| | Male | 18 | 23.5 | 23.2 | 23.9 | 24 | 23.6 | 23.6 | |
| | | 23 | 23.2 | 20.7 | 21.1 | 21.1 | 20.7 | 21.1 | 21.2 |
| | | 28 | 23.7 | 23.6 | 23.8 | 24.4 | 23.9 | 24 | 24.7 |
| | | Mean | 21.9 | 21.0 | 21.4 | 21.6 | 21.2 | 21.5 | 21.1 |
| | | SD | 1.9 | 2.0 | 2.0 | 2.1 | 2.1 | 2.2 | 2.6 |
| | | SEM | 0.8 | 0.8 | 0.8 | 0.9 | 0.9 | 1.0 | 1.3 |
| | | n | 6 | 6 | 6 | 6 | 6 | 5 | 4 |
| 200 mg/kg | Female | 4 | 19.9 | 18.7 | 18.3 | 17.9 | 18.2 | 18.4 | 18.9 |
| | | 9 | 18.8 | 18.5 | 19.2 | 19 | 18.3 | | |
| | | 14 | 19.6 | | | | | | |
| | Male | 19 | 23.6 | 23.5 | 21.5 | 22.6 | 22.7 | 23.1 | |
| | | 24 | 22.4 | 21.8 | 21.8 | 22.8 | 22.6 | 21.9 | |
| | | 29 | 21.1 | 21.6 | 21 | 21.7 | 21.7 | 21.4 | 21.9 |
| | | Mean | 20.9 | 20.8 | 20.4 | 20.8 | 20.7 | 21.2 | 20.4 |
| | | SD | 1.8 | 2.2 | 1.5 | 2.2 | 2.3 | 2.0 | 2.1 |
| | | SEM | 0.7 | 1.0 | 0.7 | 1.0 | 1.0 | 1.0 | 1.5 |
| | | n | 6 | 5 | 5 | 5 | 5 | 4 | 2 |
| 300 mg/kg | Female | 5 | 22.7 | 22.7 | | | | | |
| | | 10 | 20.6 | | | | | | |
| | | 15 | 19.1 | 19.1 | 18.6 | 19.1 | 18.9 | 18.9 | 19 |
| | Male | 20 | 21.6 | 19.9 | 20.1 | 20.4 | 20.3 | 20.9 | 21.1 |
| | | 25 | 23.6 | | | | | | |
| | | 30 | 21.7 | 19.1 | 19.8 | 19.6 | 20 | 20.6 | 21.2 |
| | | Mean | 21.6 | 20.2 | 19.5 | 19.7 | 19.7 | 20.1 | 20.4 |
| | | SD | 1.6 | 1.7 | 0.8 | 0.7 | 0.7 | 1.1 | 1.2 |
| | | SEM | 0.6 | 0.9 | 0.5 | 0.4 | 0.4 | 0.6 | 0.7 |
| | | n | 6 | 4 | 3 | 3 | 3 | 3 | 3 |

Intravenous Dosing.

Figure 9:
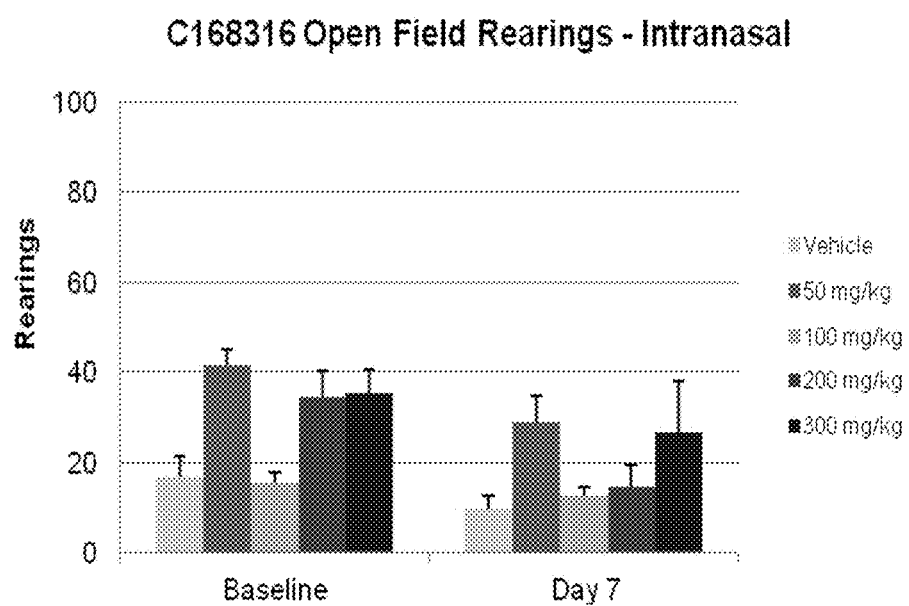
FIG. 9 Open field rearings. Group mean+SEM. *p<0.05 vs. respective vehicle group.

There were no differences in body weight between the treatment groups at any of the time points (p>0.05) (Table 2). Groups 50, 100 and 200 mg/kg were not used in statistical analysis due to mortality and low animal numbers. In total 8 mice were lost from the following treatment groups: 1 mouse from 25 mg/kg group (12.5%), 3 mice from 50 mg/kg group (75%)(treatment was discontinued for one remaining mouse in 50 mg/kg group), 2 mice from 200 mg/kg group (100%), and 2 mice from 300 mg/kg group (100%).

values than vehicle group and 50, 200 and 300 mg/kg groups had higher rearing values than vehicle group (FIG. 9).

Intravenous Dosing.

Groups 50, 100 and 200 mg/kg were not used in statistical analysis due to mortality and low animal numbers. Open field measurements were performed at baseline and on day 7. There were no differences in open field distance, rearings, distance in center, rearings in center or velocity between the treatment groups at baseline or on day 7 (p<0.05, for all) (FIGS. 13-17).

TABLE 2

Body weight in intravenous dosing groups

| Treatment | Gender | Mouse ID | Day 1 | 2 | 3 | 4 | 5 | 6 | 7 |
|---|---|---|---|---|---|---|---|---|---|
| Vehicle | Female | 31 | 19.3 | 18.8 | 19.2 | 19.7 | 19.8 | 19.7 | 19.6 |
| | | 42 | 18.7 | 18.5 | 18.4 | 18.1 | 18.4 | 18.4 | 18.3 |
| | Male | 46 | 23.4 | 23.4 | 23.4 | 23.7 | 23.7 | 23.7 | 23.6 |
| | | 49 | 21.2 | 20.7 | 21.6 | 21 | 21 | 21.4 | 21.7 |
| | | 50 | 25.8 | 25.6 | 26.1 | 26.1 | 26.1 | 26.0 | 25.9 |
| | | 54 | 24.9 | 24.2 | 24.5 | 24.6 | 24.6 | 24.6 | 24.6 |
| | | 59 | 21.7 | 21.1 | 21.5 | 21.4 | 21.4 | 21.9 | 22.3 |
| | | Mean | 22.6 | 22.3 | 22.6 | 22.5 | 22.5 | 22.6 | 22.7 |
| | | SD | 2.6 | 2.6 | 2.7 | 2.9 | 2.8 | 2.7 | 2.7 |
| | | SEM | 1.1 | 1.1 | 1.1 | 1.2 | 1.1 | 1.1 | 1.1 |
| | | n | 6 | 6 | 6 | 6 | 6 | 6 | 6 |
| 12.5 mg/kg | Female | 36 | 18.9 | 18.1 | 18.7 | 18.5 | 18.8 | 18.8 | 18.8 |
| | | 37 | 19.6 | 19.1 | 19.7 | 19.7 | 20.5 | 20.8 | 21 |
| | Male | 47 | 21.7 | 21 | 21.7 | 21.8 | 21.8 | 22.1 | 22.3 |
| | | 51 | 26.9 | 25.8 | 27.1 | 26.9 | 26.9 | 27.1 | 27.2 |
| | | 55 | 21.9 | 20.8 | 21.2 | 21.4 | 21.4 | 22.0 | 22.5 |
| | | 57 | 23.4 | 22.9 | 23.3 | 23.4 | 23.4 | 23.8 | 24.1 |
| | | 60 | 22.8 | 22.3 | 22.4 | 22.3 | 22.3 | 22.5 | 22.6 |
| | | Mean | 22.2 | 21.4 | 22.0 | 22.0 | 22.2 | 22.4 | 22.6 |
| | | SD | 2.6 | 2.6 | 2.7 | 2.7 | 2.5 | 2.6 | 2.6 |
| | | SEM | 1.0 | 1.0 | 1.0 | 1.0 | 1.0 | 1.0 | 1.0 |
| | | n | 7 | 7 | 7 | 7 | 7 | 7 | 7 |
| 25 mg/kg | Female | 40 | 21.3 | 20 | 20.4 | 20.8 | | | |
| | | 41 | 18 | 17.6 | 17.9 | 17.9 | 18.4 | 18.3 | 18.1 |
| | | 43 | 17.5 | 17.3 | 17.4 | 17.4 | 17.8 | 17.8 | 17.8 |
| | Male | 48 | 22.9 | 21.9 | 22.4 | 22.2 | 22.2 | 22.4 | 22.6 |
| | | 52 | 24.4 | 23.3 | 24.1 | 23.9 | 23.9 | 23.9 | 23.9 |
| | | 53 | 24.7 | 23.1 | 23.8 | 24 | 24 | 23.9 | 23.8 |
| | | 56 | 21.1 | 20.3 | 20.8 | 20.6 | 20.6 | 21.0 | 21.3 |
| | | 58 | 25.5 | 24.5 | 25.7 | 25.8 | 25.8 | 26.3 | 26.8 |
| | | Mean | 21.9 | 21.0 | 21.6 | 21.6 | 21.8 | 21.9 | 22.0 |
| | | SD | 3.0 | 2.7 | 3.0 | 3.0 | 3.0 | 3.1 | 3.3 |
| | | SEM | 1.1 | 0.9 | 1.1 | 1.1 | 1.1 | 1.2 | 1.2 |
| | | n | 8 | 8 | 8 | 8 | 7 | 7 | 7 |
| 50 mg/kg | Female | 38 | 16.6 | 16.1 | 16.3 | 16.2 | 16.8 | 16.8 | 16.8 |
| | | 39 | 21.4 | | | | | | |
| | | 44 | 22.8 | | | | | | |
| | | 45 | 21.2 | | | | | | |
| | | Mean | 20.5 | 16.1 | 16.3 | 16.2 | 16.8 | 16.8 | 16.8 |
| | | SD | 2.7 | | | | | | |
| | | SEM | 1.3 | | | | | | |
| | | n | 4 | 1 | 1 | 1 | 1 | 1 | 1 |

Note.
Body weight values on day 6 were not measured due to a human error. Day 6 value has been replaced by mean of days 5 and 7.

Open Field

Intranasal Dosing.

Open field measurements were performed at baseline and on day 7. There were no differences in open field distance, rearings, distance in center, rearings in center or velocity between the treatment groups on day 7 (p<0.05, for all) (FIGS. 8-12).

Figure 10:
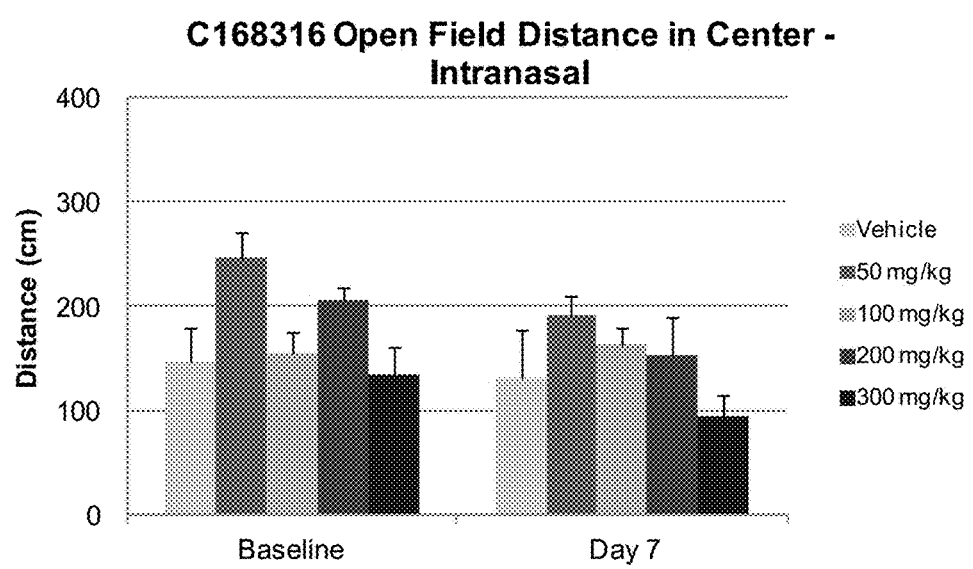
FIG. 10 Open field distance in center. Group mean+SEM. *p<0.05 vs. respective vehicle group.
Figure 11:
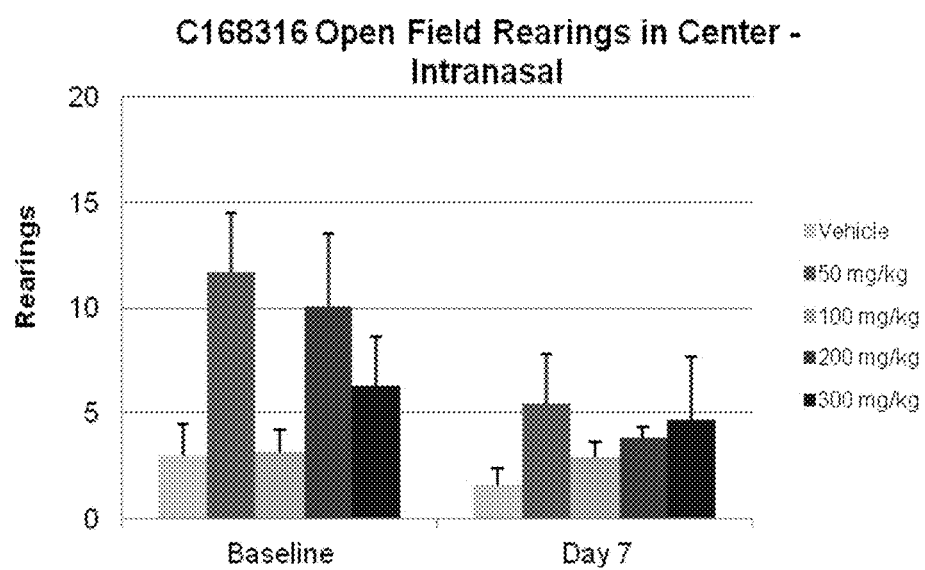
FIG. 11 Open field rearings in center. Group mean+SEM. No differences.
Figure 12:
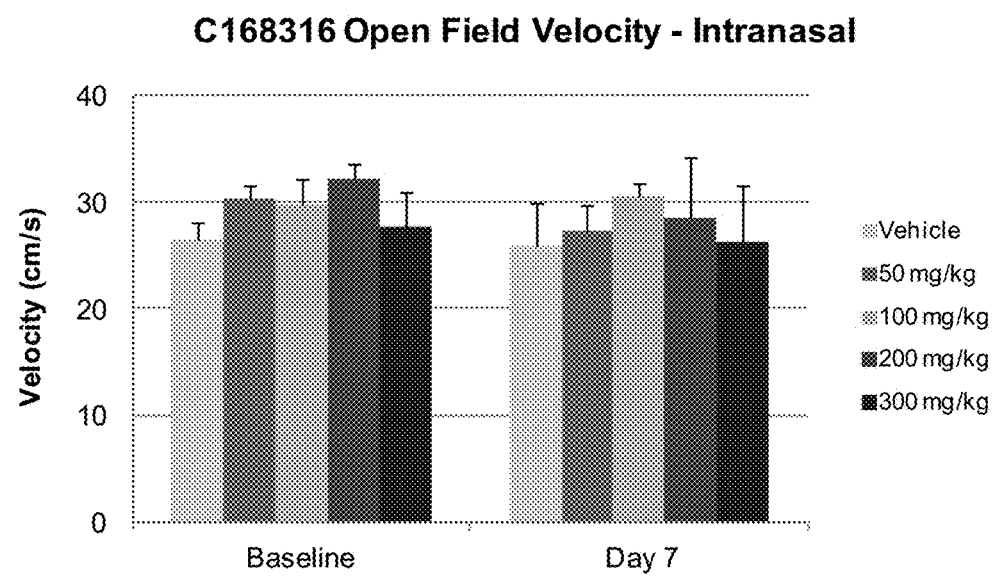
FIG. 12 Open field velocity. Group mean+SEM. No differences.
Figure 13:
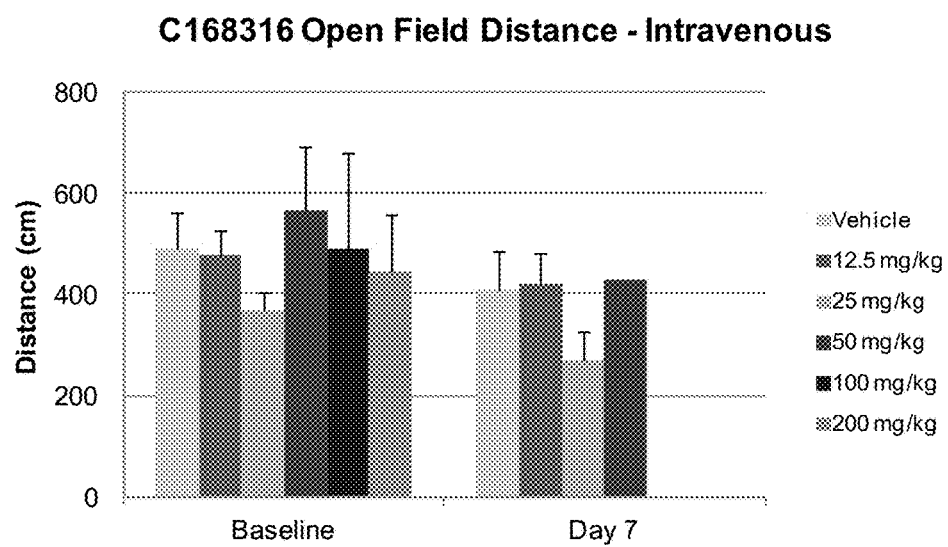
FIG. 13 Open field distance. Group mean+SEM. No differences.
Figure 14:
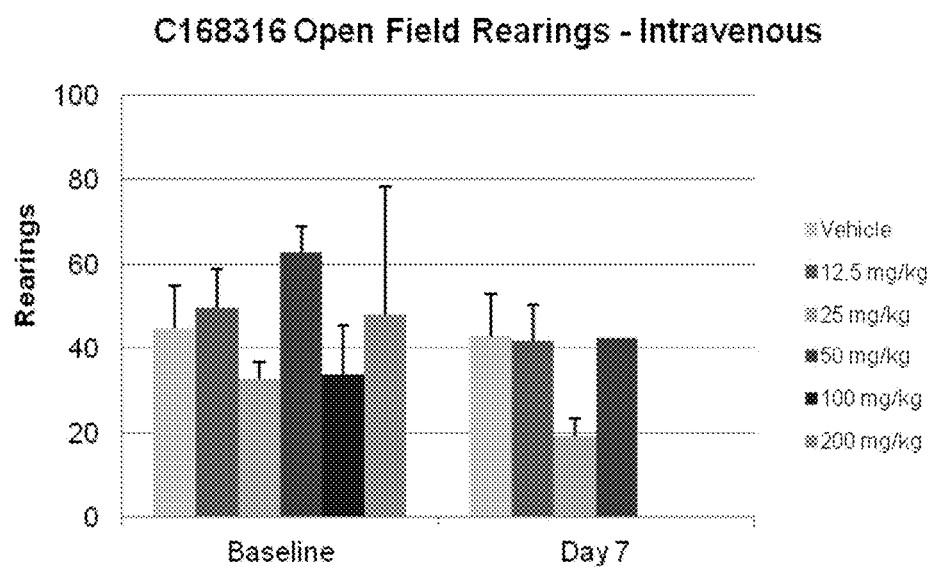
FIG. 14 Open field rearings. Group mean+SEM. No differences.
Figure 15:
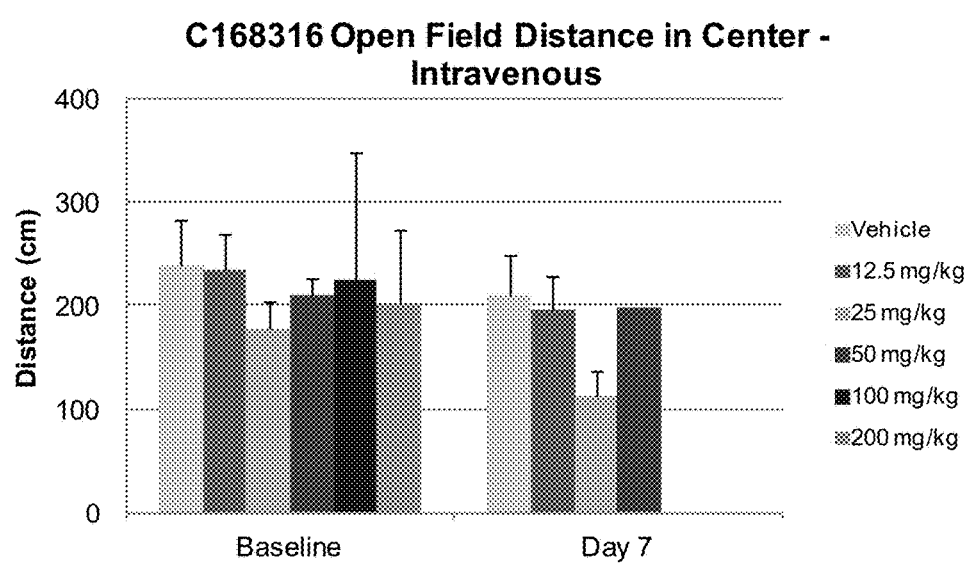
FIG. 15 Open field distance in center. Group mean+SEM. No differences.
Figure 16:
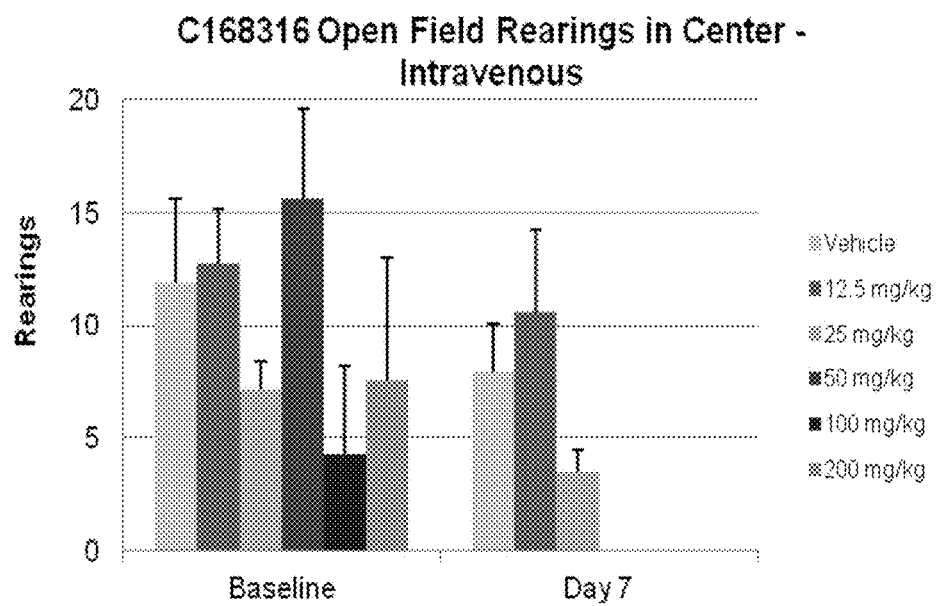
FIG. 16 Open field rearings in center. Group mean+SEM. No differences.
Figure 17:
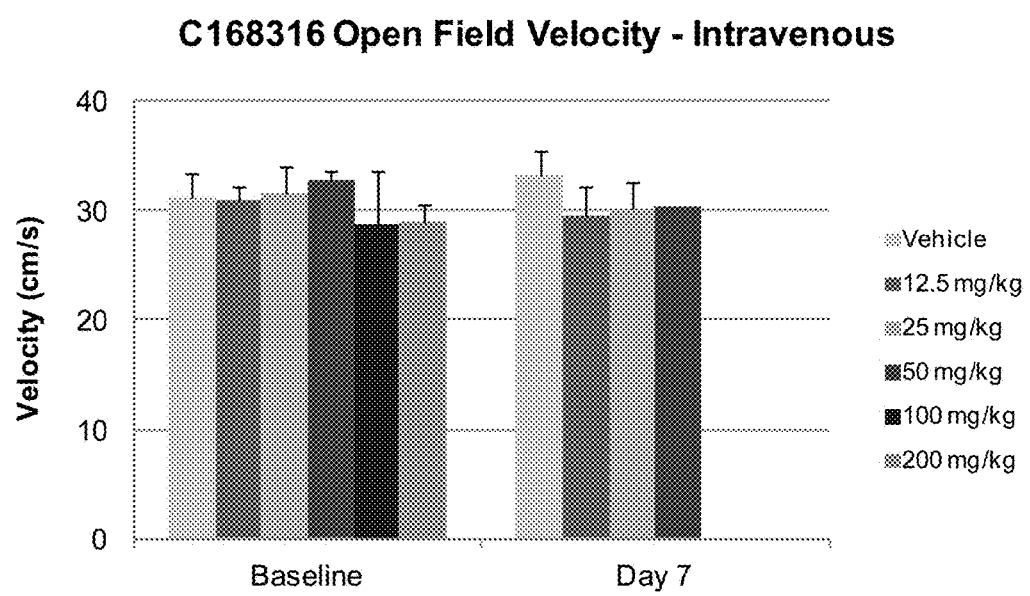
FIG. 17 Open field velocity. Group mean+SEM. No differences.

However, at baseline measurement 50 mg/kg group had higher distance (FIG. 8) and distance in center (FIG. 10)

Neurological Index

Intranasal Dosing.

Figure 18:
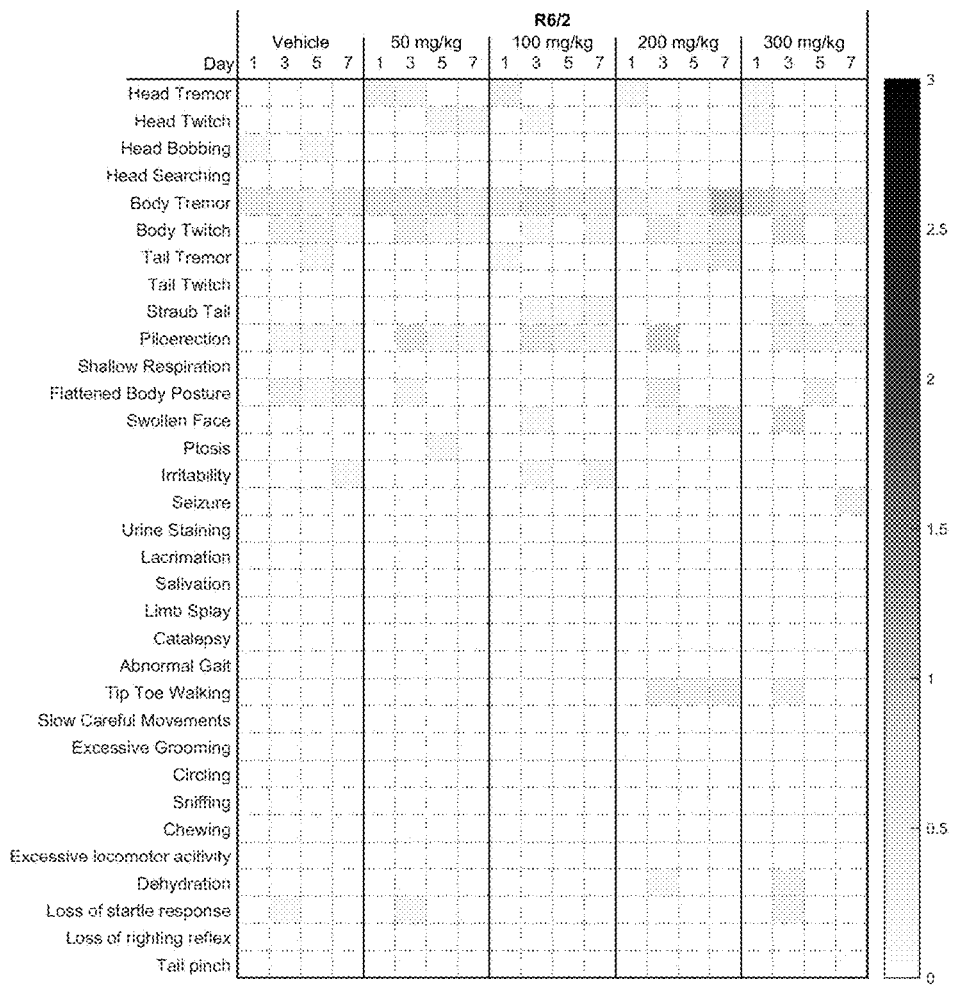
FIG. 18 Neurological index score table—intranasal dosing. 300 mg/kg group differed significantly from vehicle group on day 3*p<0.05.

The effects of intranasal dosing on neurological index score are presented in FIG. 18. When the mean score of all parameters was analyzed, a significant difference was found on day 3; 300 mg/kg treatment group had significantly higher mean score on day 3 compared to vehicle group (p<0.05).

Intravenous Dosing.

Figure 19:
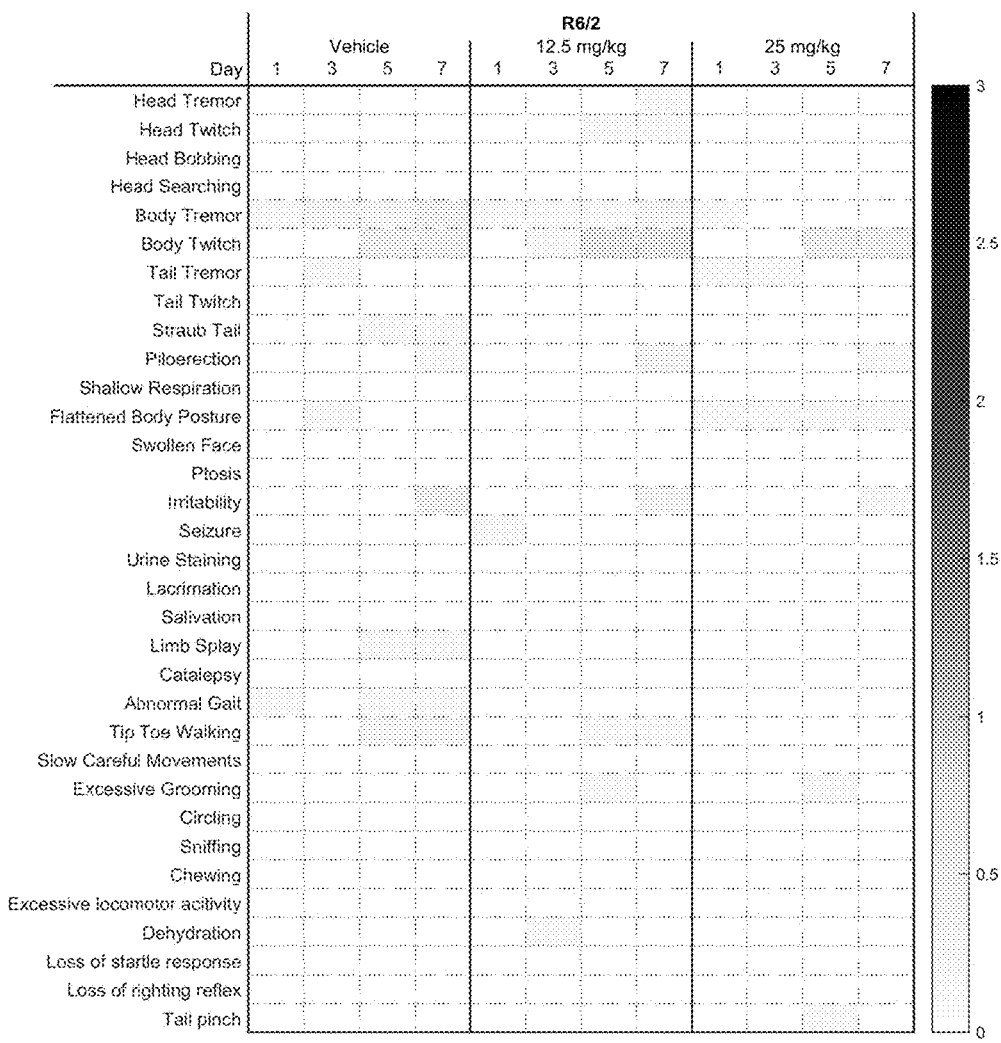
FIG. 19 Neurological index score table—intranasal dosing. No differences.
Figure 21:
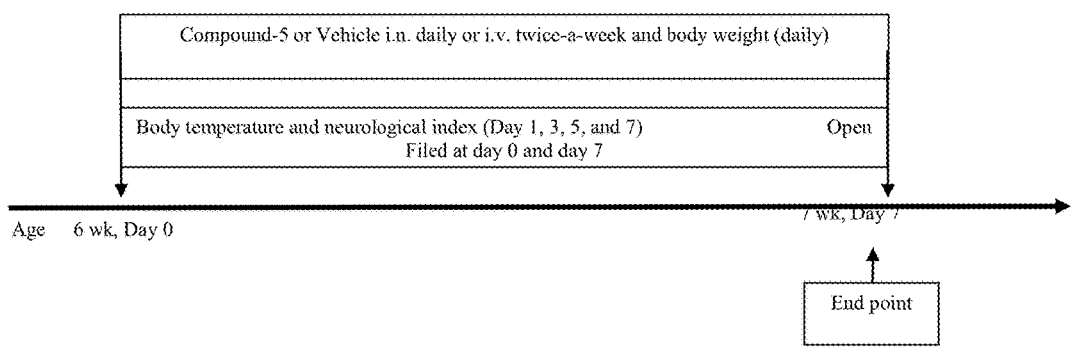
FIG. 21 Shows a timeline of study in Example 1.

There were no differences in neurological index score between the intravenous treatment groups (FIG. 19).

Body Temperature

Intranasal Dosing.

Body temperature was increased in 300 mg/kg group at baseline on day 1 (before treatment) ($p<0.05$). On day 7 the body temperature was increased in both 100 and 300 mg/kg treatment groups compared to vehicle ($p<0.05$) (Table 3).

TABLE 3

Body temperature in intranasal dosing groups

| Treatment | Gender | Mouse ID | Day 1 | Day 3 | Day 5 | Day 7 |
|---|---|---|---|---|---|---|
| Vehicle | Female | 1 | 37.3 | 37.4 | 37.8 | 37 |
| | | 6 | 35.6 | 37.8 | 36.7 | 36.2 |
| | | 11 | 36.8 | 36.5 | 37.7 | 36.5 |
| | Male | 16 | 36.1 | 35.7 | 37.3 | 36.8 |
| | | 21 | 36.3 | 36.2 | 37.7 | 36.3 |
| | | 26 | 36.1 | 35.5 | 37.3 | 36.8 |
| | Mean | | 36.4 | 36.5 | 37.4 | 36.6 |
| | SD | | 0.6 | 0.9 | 0.4 | 0.3 |
| | SEM | | 0.2 | 0.4 | 0.2 | 0.1 |
| | n | | 6 | 6 | 6 | 6 |
| 50 mg/kg | Female | 2 | 37.6 | 38.3 | 37.5 | 37.6 |
| | | 7 | 37 | | | |
| | | 12 | 37.6 | 36.9 | 37.3 | 37 |
| | Male | 17 | 35.9 | 35.8 | 36.8 | 38.1 |
| | | 22 | 36.8 | 37 | 37.2 | 36.3 |
| | | 27 | 36.4 | 36.7 | 37.9 | 37.2 |
| | Mean | | 36.9 | 36.9 | 37.3 | 37.2 |
| | SD | | 0.7 | 0.9 | 0.4 | 0.7 |
| | SEM | | 0.3 | 0.4 | 0.2 | 0.3 |
| | n | | 6 | 5 | 5 | 5 |
| 100 mg/kg | Female | 3 | 37.8 | 37.7 | 37.7 | 38.1 |
| | | 8 | 36.5 | 37.3 | 36.6 | |
| | | 13 | 37.6 | 37.3 | 37.9 | 37.7 |
| | Male | 18 | 37.4 | 37.1 | 36.9 | |
| | | 23 | 36.2 | 37 | 37.7 | 37.3 |
| | | 28 | 36.2 | 36.9 | 37.4 | 36.9 |
| | Mean | | 37.0 | 37.2 | 37.4 | 37.5 |
| | SD | | 0.7 | 0.3 | 0.5 | 0.5 |
| | SEM | | 0.3 | 0.1 | 0.2 | 0.3 |
| | n | | 6 | 6 | 6 | 4 |
| 200 mg/kg | Female | 4 | 37.3 | 37.6 | 37.8 | 37.3 |
| | | 9 | 36.9 | 37.5 | 36.7 | |
| | | 14 | 37.7 | | | |
| | Male | 19 | 36.8 | 36.6 | 37.4 | |
| | | 24 | 36.9 | 37.2 | 38 | |
| | | 29 | 37.4 | 37.1 | 38.3 | 37.5 |
| | Mean | | 37.2 | 37.2 | 37.6 | 37.4 |
| | SD | | 0.4 | 0.4 | 0.6 | 0.1 |
| | SEM | | 0.1 | 0.2 | 0.3 | 0.1 |
| | n | | 6 | 5 | 5 | 2 |
| 300 mg/kg | Female | 5 | 37.5 | | | |
| | | 10 | 37.1 | | | |
| | | 15 | 37.8 | 37.3 | 37.6 | 37.9 |
| | Male | 20 | 37.6 | 37.2 | 38 | 37.6 |
| | | 25 | 37.2 | | | |
| | | 30 | 37.5 | 36.7 | 37.1 | 37.3 |
| | Mean | | 37.5 | 37.1 | 37.6 | 37.6 |
| | SD | | 0.3 | 0.3 | 0.5 | 0.3 |
| | SEM | | 0.1 | 0.2 | 0.3 | 0.2 |
| | n | | 6 | 3 | 3 | 3 |

Intravenous Dosing.

There were no significant differences between the intravenous treatment groups in body temperature ($p>0.05$) (Table 4).

TABLE 4

Body temperature in intravenous dosing groups

| Treatment | Gender | Mouse ID | Day 1 | Day 3 | Day 5 | Day 7 |
|---|---|---|---|---|---|---|
| Vehicle | Female | 31 | 37.5 | 37.8 | 37.1 | 38.1 |
| | | 42 | 37.2 | 38 | 38.3 | 38 |
| | Male | 46 | 36.7 | 36.5 | 36.6 | 35.8 |
| | | 49 | 37.3 | 37.3 | 36.7 | 36.9 |
| | | 50 | 38.6 | 37.8 | 37.9 | 37.6 |
| | | 54 | 36.7 | 37.7 | 37.1 | 37.7 |
| | | 59 | 37.3 | 36.9 | 37.4 | 38.2 |
| | Mean | | 37.3 | 37.4 | 37.3 | 37.5 |
| | SD | | 0.6 | 0.6 | 0.6 | 0.9 |
| | SEM | | 0.2 | 0.2 | 0.2 | 0.3 |
| | n | | 7 | 7 | 7 | 7 |
| 12.5 mg/kg | Female | 36 | 37.1 | 38 | 37.3 | 37.4 |
| | | 37 | 37.2 | 37.3 | 37.1 | 37 |
| | Male | 47 | 36.3 | 36.5 | 37.2 | 37.3 |
| | | 51 | 35.7 | 37.2 | 36.2 | 37.2 |
| | | 55 | 36.3 | 37.8 | 37 | 38.3 |
| | | 57 | 37.1 | 36.8 | 36.5 | 37.5 |
| | | 60 | 37 | 37.6 | 37.6 | 38.6 |
| | Mean | | 36.7 | 37.3 | 37.0 | 37.6 |
| | SD | | 0.6 | 0.5 | 0.5 | 0.6 |
| | SEM | | 0.2 | 0.2 | 0.2 | 0.2 |
| | n | | 7 | 7 | 7 | 7 |
| 25 mg/kg | Female | 40 | 37.9 | 37.8 | | |
| | | 41 | 36.6 | 36.8 | 36.7 | 36.7 |
| | | 43 | 36.4 | 36.9 | 37.9 | 37.4 |
| | Male | 48 | 38.5 | 37.6 | 37.9 | 37.5 |
| | | 52 | 36.3 | 37.1 | 37.2 | 36.8 |
| | | 53 | 36.3 | 36.8 | 36.3 | 37.9 |
| | | 56 | 37.1 | 37.6 | 36.3 | 37.6 |
| | | 58 | 37.1 | 36.6 | 37.3 | 37.5 |
| | Mean | | 37.0 | 37.2 | 37.1 | 37.3 |
| | SD | | 0.8 | 0.5 | 0.7 | 0.4 |
| | SEM | | 0.3 | 0.2 | 0.3 | 0.2 |
| | n | | 8 | 8 | 7 | 7 |
| 50 mg/kg | Female | 38 | 37.4 | 37.7 | 38 | 37 |
| | | 39 | 38.1 | | | |
| | | 44 | 37.1 | | | |
| | | 45 | 37.5 | | | |
| | Mean | | 37.5 | 37.7 | 38.0 | 37.0 |
| | SD | | 0.4 | | | |
| | SEM | | 0.2 | | | |
| | n | | 4 | 1 | 1 | 1 |

CONCLUSIONS

These results show that both intranasal and intravenous treatment with Compound-5 in R6/2 mice of Huntington's disease increase mortality in dose-dependent manner. The compound has no effect on movement activity in open field test on day 7 post-dosing. However, intranasal dosing of Compound-5 increased neurological index score and body temperature. These result suggest that the highest tolerated dose for Compound-5 could be 50-100 mg/kg intranasally and 12.5-25 mg/kg intravenously.

All patents, patent applications, and other publications, including GenBank Accession Numbers, cited in this application are incorporated by reference in the entirety for all purposes.

REFERENCES

1. Orr H T (2012) Polyglutamine neurodegeneration: expanded glutamines enhance native functions. *Curr Opin Genet Dev* 22(3):251-5.
2. Fan H C, Ho L I, Chi C S, Chen S J, Peng G S, Chan T M, Lin S Z, Ham H J (2014) Polyglutamine (PolyQ) diseases: genetics to treatments. *Cell Transplant* 23(4-5): 441-58.

3. Andreassen O A, Dedeoglu A, Ferrante R J, Jenkins B G, Ferrante K L, Thomas M, Friedlich A, Browne S E, Schilling G, Borchelt D R, Hersch S M, Ross C A, Beal M F (2001) Creatine increase survival and delays motor symptoms in a transgenic animal model of Huntington's disease. *Neurobiol Dis* 8(3):479-91.
4. D'Abreu A, Franca M C Jr, Paulson H L, Lopes-Cendes I (2010) Caring for Machado-Joseph disease: current understanding and how to help patients. *Parkinsonism Relat Disord* 16(1):2-7.
5. Takahashi T, Katada S, Onodera O (2010) Polyglutamine diseases: where does toxicity come from? what is toxicity? where are we going? *J Mol Cell Biol* 2(4):180-91.
6. Li L B, Yu Z, Teng X, Bonini N M (2008) RNA toxicity is a component of ataxin-3 degeneration in *Drosophila*. *Nature* 453(7198):1107-11.
7. Tsoi H, Lau T C, Tsang S Y, Lau K F, Chan H Y (2012) CAG expansion induces nucleolar stress in polyglutamine diseases. *Proc Natl Acad Sci USA* 109(33):13428-33.
8. Arribat Y, Bonneaud N, Talmat-Amar Y, Layalle S, Parmentier M L, Maschat F (2013) A huntingtin peptide inhibits polyQ-huntingtin associated defects. *PLoS One* 8(7):e68775.
9. Nagai Y, Tucker T, Ren H, Kenan D J, Henderson B S, Keene J D, Strittmatter W J, Burke J R (2000) Inhibition of polyglutamine protein aggregation and cell death by novel peptides identified by phage display screening. *J Biol Chem* 275(14):10437-42.
10. Sánchez I, Mahlke C, Yuan J (2003) Pivotal role of oligomerization in expanded polyglutamine neurodegenerative disorders. *Nature* 421(6921):373-9.
11. Kumar A, Parkesh R, Sznajder L J, Childs-Disney J L, Sobczak K, Disney M D (2012) Chemical correction of pre-mRNA splicing defects associated with sequestration of muscleblind-like 1 protein by expanded r(CAG)-containing transcripts. *ACS Chem Biol* 7(3):496-505.
12. Marcheschi R J, Tonelli M, Kumar A, Butcher S E (2011) Structure of the HIV-1 frameshift site RNA bound to a small molecule inhibitor of viral replication. *ACS Chem Biol* 6(8):857-64.
13. Lee F K, Wong A K, Lee Y W, Wan O W, Chan H Y, Chung K K (2009) The role of ubiquitin linkages on alpha-synuclein induced-toxicity in a *Drosophila* model of Parkinson's disease. *J Neurochem* 110(1):208-19.
14. Garcia-Lopez A, Monferrer L, Garcia-Alcover I, Vicente-Crespo M, Alvarez-Abril M C, Artero R D (2008) Genetic and chemical modifiers of a CUG toxicity model in *Drosophila*. *PLoS One* 3(2):e1595.
15. Jin P, Zarnescu D C, Zhang F, Pearson C E, Lucchesi J C, Moses K, Warren S T (2003) RNA-mediated neurodegeneration caused by the fragile X premutation rCGG repeats in *Drosophila*. *Neuron* 39(5):739-47.
16. Bañez-Coronel M, Porta S, Kagerbauer B, Mateu-Huertas E, Pantano L, Ferrer I, Guzmán M, Estivill X, Marti E (2012) A pathogenic mechanism in Huntington's disease involves small CAG-repeated RNAs with neurotoxic activity. *PLoS Genet* 8(2):e1002481.
17. Wong C H, Nguyen L, Peh J, Luu L M, Sanchez J S, Richardson S L, Tuccinardi T, Tsoi H, Chan W Y, Chan H Y, Baranger A M, Hergenrother P J, Zimmerman S C (2014) Targeting toxic RNAs that cause myotonic dystrophy type 1 (DM1) with a bisamidinium inhibitor. *J Am Chem Soc* 136(17):6355-61.
18. Wong S L, Chan W M, Chan H Y (2008) Sodium dodecyl sulfate-insoluble oligomers are involved in polyglutamine degeneration. *Faseb J* 22(9), 3348-57.

What is claimed is:

1. A method for inhibiting a polyglutamine (polyQ) disease in a subject, comprising administering to the subject an effective amount of a compound of formula I:

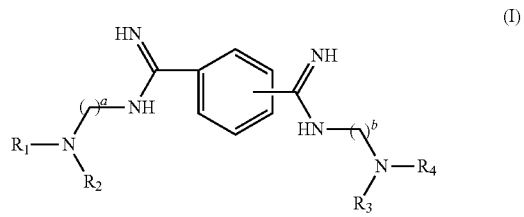

(I)

or a pharmaceutically acceptable salt, racemate, enantiomer, diastereomer, poly-morph, tautomer, geometric isomer, or prodrug thereof;
wherein $R^1$, $R^2$, $R^3$, and $R^4$ are each independently hydrogen, $C_{1-8}$ alkyl, of substituted $C_{1-8}$ alkyl; and subscripts a and b are each independently an integer from 1 to 8.

2. The method of claim 1, wherein the compound is one of formula II:

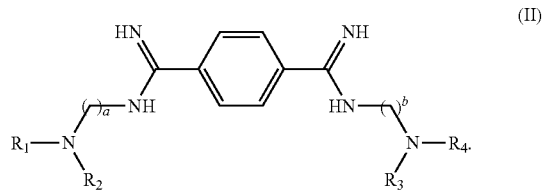

(II)

3. The method of claim 1, wherein the compound is one of formula III:

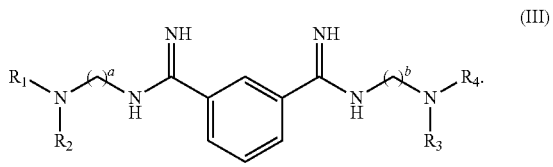

(III)

4. The method of any one of claims 1-3, wherein the compound inhibits expanded CAG-RNA mediated toxicity in an in vitro or in vivo assay.

5. The method of claim 1, wherein the compound is DB213, DB213_D1, DB213_D2, DB213_D3, DB213_D4, DB213_D5, DB213_D6, or DB213_D7:

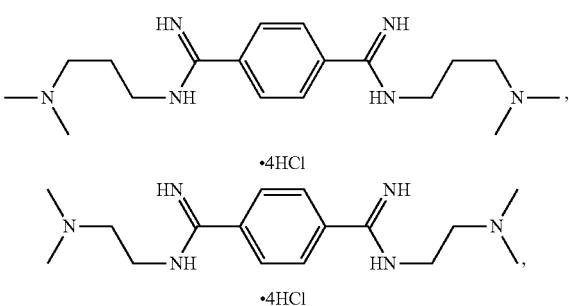

-continued

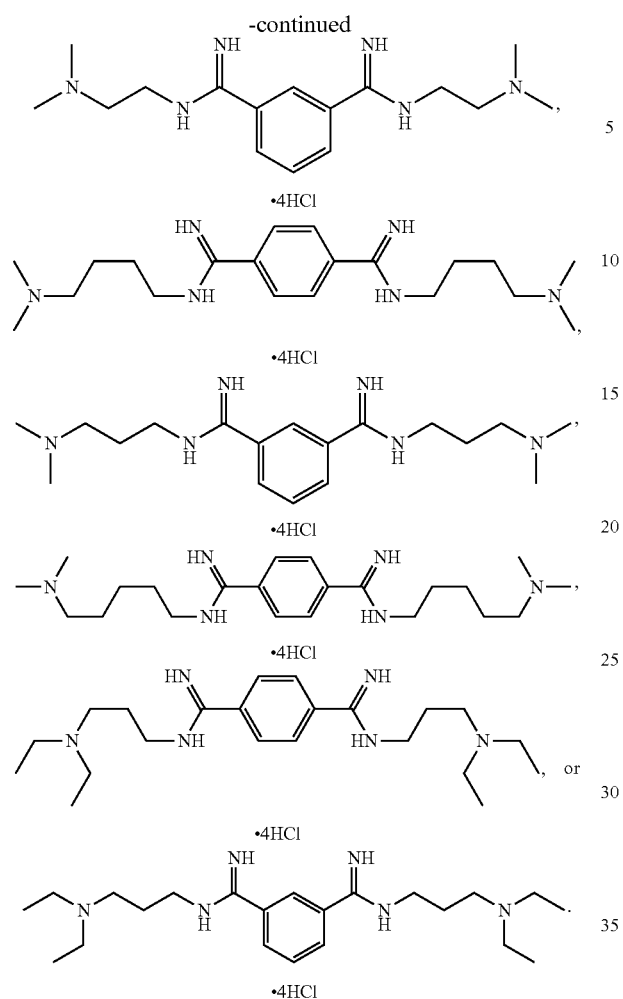

6. The method of claim 1, wherein the compound is DB213:

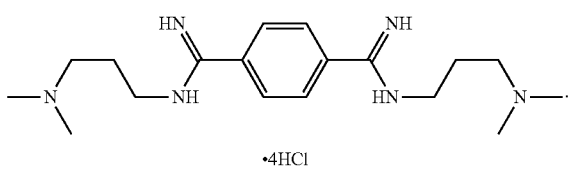

7. The method of claim 1, wherein the compound is administered with another therapeutic agent effective for treating a polyQ disease.

8. The method of claim 1, wherein the compound is administered orally, intravenously, intramuscularly, or subcutaneously.

9. The method of claim 1, wherein the subject has been diagnosed with a polyQ disease or is at risk of developing a polyQ disease.

10. The method of claim 1, wherein the compound is administered once daily, weekly, or monthly.

11. The method of claim 1, wherein about 1-10,000 mg, about 10-1,000 mg, about 10-100 mg, about 20-50 mg, or about 10, 20, 30, 40, or 50 mg of the compound is administered each time to the subject per kg of the subject's body weight.

12. A kit for treating a polyQ disease, comprising a container containing a pharmaceutical composition comprising a compound of formula I:

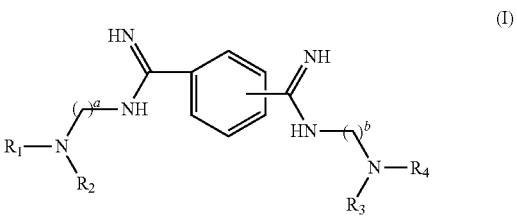

or a pharmaceutically acceptable salt, racemate, enantiomer, diastereomer, poly-morph, tautomer, geometric isomer, or prodrug thereof;
wherein $R^1$, $R^2$, $R^3$, and $R^4$ are each independently hydrogen, $C_{1-8}$ alkyl, of substituted $C_{1-8}$ alkyl; and subscripts a and b are each independently an integer from 1 to 8.

13. The kit of claim 12, wherein the compound is one of formula II:

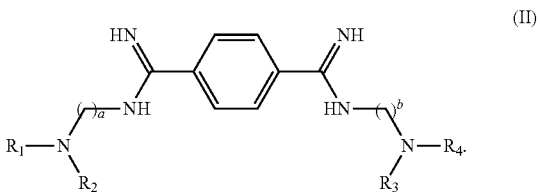

14. The kit of claim 12, wherein the compound is one of formula III:

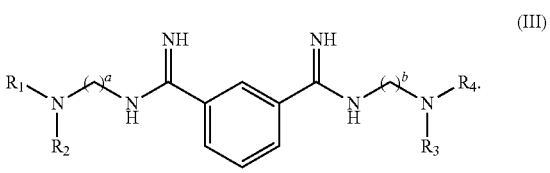

15. The kit of any one of claims 12-14, wherein the compound inhibits expanded CAG-RNA mediated toxicity in an in vitro or in vivo assay.

16. The kit of claim 14, wherein the compound is DB213, DB213_D1, DB213_D2, DB213_D3, DB213_D4, DB213_D5, DB213_D6, or DB213_D7:

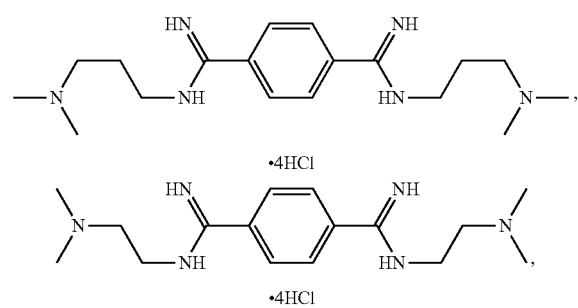

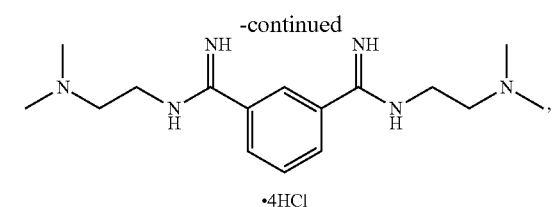
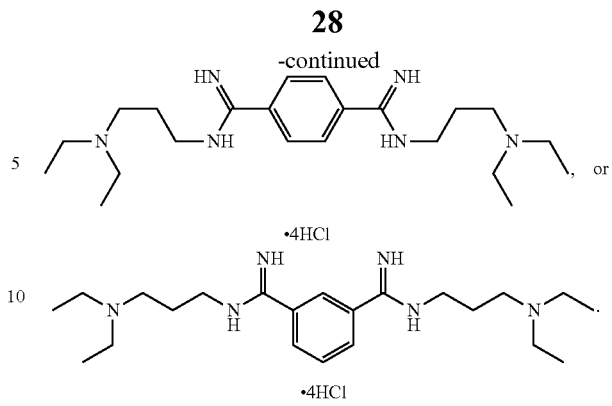
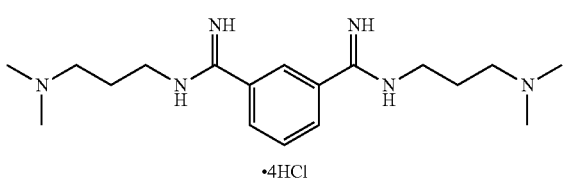
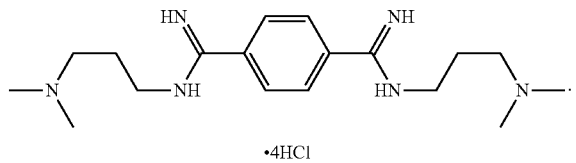
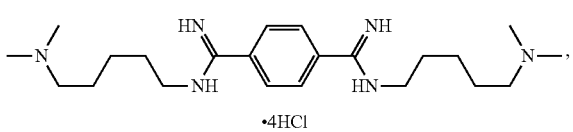
17. The kit of claim 16, wherein the compound is DB213:
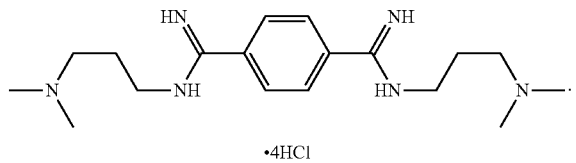
18. The kit of claim 12, further comprising a second pharmaceutical composition comprising a second compound effective for treating a polyQ disease.
19. The kit of claim 12, further comprising informational material providing instructions on administration of the pharmaceutical composition.
* * * * *